United States Patent [19]

Christensen, IV et al.

[11] Patent Number: 6,118,017
[45] Date of Patent: Sep. 12, 2000

[54] SUBSTITUTED-(3-CYCLOPENTYLOXY-4-METHOXYPHENYL)-3-PHENYLCYANOCYCLOBUTAN-1-ONE

[75] Inventors: Siegfried B. Christensen, IV, Philadelphia, Pa.; Cornelia J. Forster, Pelham, N.H.

[73] Assignee: SmithKline Beecham Corporation, Philadelphia, Pa.

[21] Appl. No.: 09/291,576

[22] Filed: Apr. 8, 1999

Related U.S. Application Data

[60] Provisional application No. 60/081,643, Apr. 14, 1998.

[51] Int. Cl.[7] .................... C07C 255/00; C07C 229/00; C07C 249/00; C07C 205/00; C07C 49/23
[52] U.S. Cl. ............................ 558/426; 560/35; 560/51; 560/55; 564/271; 568/306; 568/329; 568/330; 514/520; 514/523; 514/532; 514/541; 514/641; 514/676; 514/683; 514/684
[58] Field of Search ..................... 568/306, 329, 568/350; 564/271; 514/641, 676, 683, 684, 520, 532, 541, 523; 558/426; 560/35, 51, 55

[56] References Cited

U.S. PATENT DOCUMENTS

| | | | |
|---|---|---|---|
| 5,187,192 | 2/1993 | Brooks et al. | 514/445 |
| 5,362,915 | 11/1994 | Maschler et al. | 568/20 |
| 5,552,438 | 9/1996 | Christensen . | |
| 5,712,298 | 1/1998 | Amschler | 514/352 |
| 5,883,106 | 3/1999 | Stevens et al. | 514/277 |

OTHER PUBLICATIONS

Honda et al, "Chiral synthesis of phosphodiesterase inhibitor rolipram . . .", CA 124:260749, 1996.

Honda, et al., "Chiral synthesis of phosphodiesterase inhibitor, ®–(–)–rolipra, by means of enantioselective deprotonation strategy". Heterocycles, Jan. 1996, vol. 42, No. 1, pp. 109–111, especialy p. 10.

*Primary Examiner*—Deborah C. Lambkin
*Attorney, Agent, or Firm*—James M. Kanagy; Charles M. Kinzig

[57] ABSTRACT

This invention relates to ketones, alcohols and amines and acids represented by the likes of 3-(3-cyclopentyloxy-4-methoxyphenyl)-3-phenylcyanoclobutan-1-one. They are useful as PDE 4 antngionists.

10 Claims, No Drawings

SUBSTITUTED-(3-CYCLOPENTYLOXY-4-METHOXYPHENYL)-3-PHENYLCYANOCYCLOBUTAN-1-ONE

Provisional Application No. 60/081,643 filed Apr. 14, 1998.

SCOPE OF THE INVENTION

This invention covers certain ketones, alcohols, amines, and carboxylic acids represented by the likes of 3-(3-cyclopentyloxy-4-methoxyphenyl)-3-phenylcyanocyclobutan-1-one. These ketones are selective for inhibiting the catalytic site in the phosphodiesterase isoenzyme denominated 4 (PDE 4 hereafter) while exhibiting little or no affinity for a second binding site on the PDE 4 isoenzyme denominated the high affinity rolipram binding site. A method for treating diseases related to inhibiting the catalytic site in the PDE 4 isoenzyme, e.g., asthma, COPD, etc. is also disclosed.

AREA OF THE INVENTION

Cyclic nulceotide phosphodiesterases (PDEs) represent a family of enzymes that hydrolyze the ubiquitous intracellular second messengers, adenosine 3', 5'-monophosphate (cAMP) and guanosine 3', 5'-monophosphate (cGMP) to their corresponding inactive 5'-monophosphate metabolites. At least five distinct PDE isoenzymes are believed to exist, each possessing unique physical and kinetic charactersitics and each representing a product of a different gene family. Also the distribution of these isoenzymes appears to differ markedly among cell types.

Bronchial asthma is a complex, multifactorial disease characterized by reversible narrowing of the airway and hyperreactivity of the respiratory tract to external stimuli.

Identification of novel therapeutic agents for asthma is made difficult by the fact that multiple mediators are responsible for the development of the disease. Thus, it seems unlikely that eliminating the effects of a single mediator will have a substantial effect on all three components of chronic asthma. An alternative to the "mediator approach" is to regulate the activity of the cells responsible for the pathophysiology of the disease.

One such way is by elevating levels of cAMP (adenosine cyclic 3', 5'-monophosphate). Cyclic AMP has been shown to be a second messenger mediating the biologic responses to a wide range of hormones, neurotransmitters and drugs; [Krebs Endocrinology Proceedings of the 4th International Congress Excerpta Medica, 17–29, 1973]. When the appropriate agonist binds to specific cell surface receptors, adenylate cyclase is activated, which converts $Mg^{+2}$-ATP to cAMP at an accelerated rate.

Cyclic AMP modulates the activity of most, if not all, of the cells that contribute to the pathophysiology of extrinsic (allergic) asthma. As such, an elevation of cAMP would produce beneficial effects including: 1) airway smooth muscle relaxation, 2) inhibition of mast cell mediator release, 3) suppression of neutrophil degranulation, 4) inhibition of basophil degranulation, and 5) inhibition of monocyte and macrophage activation. Hence, compounds that activate adenylate cyclase or inhibit phosphodiesterase should be effective in suppressing the inappropriate activation of airway smooth muscle and a wide variety of inflammatory cells. The principal cellular mechanism for the inactivation of cAMP is hydrolysis of the 3'-phosphodiester bond by one or more of a family of isozymes referred to as cyclic nucleotide phosphodiesterases (PDEs).

It has now been shown that a distinct cyclic nucleotide phosphodiesterase (PDE) isozyme, PDE 4, is responsible for cAMP breakdown in airway smooth muscle and inflammatory cells. [Torphy, "Phosphodiesterase Isozymes: Potential Targets for Novel Anti-asthmatic Agents" in New Drugs for Asthma, Barnes, ed. IBC Technical Services Ltd., 1989]. Research indicates that inhibition of this enzyme not only produces airway smooth muscle relaxation, but also suppresses degranulation of mast cells, basophils and neutrophils along with inhibiting the activation of monocytes and neutrophils. Moreover, the beneficial effects of PDE 4 inhibitors are markedly potentiated when adenylate cyclase activity of target cells is elevated by appropriate hormones or autocoids, as would be the case in vivo. Thus PDE 4 inhibitors would be effective in the asthmatic lung, where levels of prostaglandin $E_2$ and prostacyclin (activators of adenylate cyclase) are elevated. Such compounds would offer a unique approach toward the pharmacotherapy of bronchial asthma and possess significant therapeutic advantages over agents currently on the market.

The compounds of this invention also inhibit the production of Tumor Necrosis Factor (TNF), a serum glycoprotein. Excessive or unregulated TNF production has been implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, reperfusion injury, graft vs. host reaction, allograft rejections, fever and myalgias due to infection, such as influenza, cachexia secondary to infection or malignancy, cachexia secondary to human acquired immune deficiency syndrome (AIDS), AIDS, ARC (AIDS related complex), keloid formation, scar tissue formation, Crohn's disease, ulcerative colitis, or pyresis, in addition to a number of autoimmune diseases, such as multiple sclerosis, autoimmune diabetes and systemic lupus erythematosis.

AIDS results from the infection of T lymphocytes with Human Immunodeficiency Virus (HIV). At least three types or strains of HIV have been identified, i.e., HIV-1, HIV-2 and HIV-3. As a consequence of HIV infection, T-cell-mediated immunity is impaired and infected individuals manifest severe opportunistic infections and/or unusual neoplasms. HIV entry into the T lymphocyte requires T lymphocyte activation. Viruses such as HIV-1 or HIV-2 infect T lymphocytes after T cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication.

Cytokines, specifically TNF, are implicated in activated T-cell-mediated HIV protein expression and/or virus replication by playing a role in maintaining T lymphocyte activation. Therefore, interference with cytokine activity such as by inhibition of cytokine production, notably TNF, in an HIV-infected individual aids in limiting the maintenance of T cell activation, thereby reducing the progression of HIV infectivity to previously uninfected cells which results in a slowing or elimination of the progression of immune dysfunction caused by HIV infection. Monocytes, macrophages, and related cells, such as kupffer and glial cells, have also been implicated in maintenance of the HIV infection. These cells, like T cells, are targets for viral replication and the level of viral replication is dependent upon the activation state of the cells. [See Rosenberg et al., The Immunopathogenesis of HIV Infection, Advances in Immunology, Vol. 57, 1989]. Monokines, such as TNF, have been shown to activate HIV replication in monocytes and/or macrophages [See Poli et al., Proc. Natl. Acad. Sci., 87:782–784, 1990], therefore, inhibition of monokine production or activity aids in limiting HIV progression as stated above for T cells.

TNF has also been implicated in various roles with other viral infections, such as the cytomegalovirus (CMV), influenza virus, adenovirus, and the herpes virus for similar reasons as those noted.

TNF is also associated with yeast and fungal infections. Specifically *Candida albicans* has been shown to induce TNF production in vitro in human monocytes and natural killer cells. [See Riipi et al., Infection and Immunity, 58(9):2750–54, 1990; and Jafari et al., Journal of Infectious Diseases, 164:389–95, 1991. See also Wasan et al., Antimicrobial Agents and Chemotherapy, 35, (10):2046–48, 1991; and Luke et al., Journal of Infectious Diseases, 162:211–214,1990].

The ability to control the adverse effects of TNF is furthered by the use of the compounds which inhibit TNF in mammals who are in need of such use. There remains a need for compounds which are useful in treating TNF-mediated disease states which are exacerbated or caused by the excessive and/or unregulated production of TNF.

SUMMARY OF THE INVENTION

The novel compounds of this invention are represented by Formula (I):

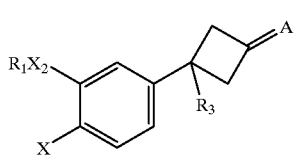

(I)

wherein:
$R_1$ is —$(CR_4R_5)_nC(O)O(CR_4R_5)_mR_6$, —$(CR_4R_5)_nC(O)NR_4(CR_4R_5)_mR_6$, —$(CR_4R_5)_nO(CR_4R_5)_mR_6$, or —$(CR_4R_5)'R_6$ wherein the alkyl moieties may be unsubstituted or substituted with one or more fluorines;

m is 0 to 2;
n is 1 to 4;
r is 0 to 6;
$R_4$ and $R_5$ are independently hydrogen or $C_{1-2}$ alkyl;
$R_6$ is hydrogen, methyl, hydroxyl, aryl, halo substituted aryl, aryloxy $C_{1-3}$ alkyl, halo substituted aryloxy $C_{1-3}$ alkyl, indanyl, indenyl, $C_{7-11}$ polycycloalkyl, tetrahydrofuranyl, furanyl, tetrahydropyranyl, pyranyl, tetrahydrothienyl, thienyl, tetrahydrothiopyranyl, thiopyranyl, $C_{3-6}$ cycloalkyl, or a $C_{4-6}$ cycloalkyl containing one or two unsaturated bonds, wherein the cycloalkyl or heterocyclic moiety may be unsubstituted or substituted by 1 to 3 methyl groups, one ethyl group or an hydroxyl group;

provided that:
a) when $R_6$ is hydroxyl, then m is 2; or
b) when $R_6$ is hydroxyl, then r is 2 to 6; or
c) when $R_6$ is 2-tetrahydropyranyl, 2-tetrahydrothiopyranyl, 2-tetrahydrofuranyl, or 2-tetrahydrothienyl, then m is 1 or 2; or
d) when $R_6$ is 2-tetrahydropyranyl, 2-tetrahydrothiopyranyl, 2-tetrahydrofuranyl, or 2-tetrahydrothienyl, then r is 1 to 6;
e) when n is 1 and m is 0, then $R_6$ is other than H in —$(CR_4R_5)_nO(CR_4R_5)_mR_6$;

X is $VR_2$, halogen, nitro, $NR_4R_5$, or formyl amine;
V is O or $S(O)m'$;
m' is 0, 1, or 2;
$X_2$ is O or $NR_8$;
$R_2$ is —$CH_3$ or —$CH_2CH_3$ unsubstituted or substituted by 1 or more fluorines;
$R_3$ is hydrogen, halogen, $C_{1-4}$ alkyl, halo-substituted $C_{1-4}$ alkyl, $CH_2NHC(O)C(O)NH_2$, —CH=$CR_8{'}R_8{'}$, cyclopropyl optionally substituted by $R_8{'}$, CN, $OR_8$, $CH_2OR_8$, $NR_8R_{10}$, $CH_2NR_8R_{10}$, C(Z)H, C(O)$OR_8$, C(O)$NR_8R_{10}$, or C≡$CR_8$.

Z is O, $NR_9$, $NOR_8$, NCN, C(—$CN)_2$, $CR_8CN$, $CR_8NO_2$, $CR_8C(O)OR_8$, $CR_8C(O)NR_8R_8$, C(—CN)$NO_2$, C(—CN)C(O)$OR_9$, C(—CN)C(O)$NR_8R_8$;

A is O, $NR_7$, $NCR_4R_5C_{2-6}$ alkenyl, $NOR_{14}$, $NOR_{15}$, $NOCR_4R_5C_{2-6}$ alkenyl, $NNR_4R_{14}$, $NNR_4R_{15}$, NCN, $NNR_8C(O)NR_8R_{14}$, $NNR_8C(S)NR_8R_{14}$, or =A is 2-(1,3-dithiane), 2-(1,3-dithiolane), dimethylthio ketal, diethylthio ketal, 2-(1,3-dioxolane), 2(1,3-dioxane), 2-(1,3-oxathiolane), dimethyl ketal or diethyl ketal;

$R_7$ is —$(CR_4R_5)_qR_{12}$ or $C_{1-6}$ alkyl wherein the $R_{12}$ or $C_{1-6}$ alkyl group is unsubstituted or substituted one or more times by methyl or ethyl unsubstituted or substituted by 1–3 fluorines, —F, —Br, —Cl, —$NO_2$, —$NR_{10}R_{11}$, —$C(O)R_8$, —$CO_2R_8$, —$O(CH_2)_qR_8$, —CN, —$C(O)NR_{10}R_{11}$, —$O(CH_2)_qC(O)NR_{10}R_{11}$, —$O(CH_2)_qC(O)R_8$, —$NR_{10}C(O)NR_{10}R_{11}$, —$NR_{10}C(O)R_{11}$, —$NR_{10}C(O)OR_9$, —$NR_{10}C(O)R_{13}$, —$C(NR_{10})NR_{10}R_{11}$, —C(NCN)$NR_{10}R_{11}$, —C(NCN)$SR_9$, —$NR_{10}$C(NCN)$SR_9$, —$NR_{10}$C(NCN)$NR_{10}R_{11}$, —$NR_{10}S(O)_2R_9$, —$S(O)_{m'}R_9$, —$NR_{10}C(O)C(O)NR_{10}R_{11}$, —$NR_{10}C(O)C(O)R_{10}$, or $R_{13}$;

q is 0, 1, or 2;
$R_{12}$ is $R_{13}$, $C_3$–$C_7$ cycloalkyl, (2-, 3- or 4-pyridyl), pyrimidyl, pyrazolyl, (1- or 2-niidazolyl), pyrrolyl, piperazinyl, piperidinyl, morpholinyl, furanyl, (2- or 3-thienyl), uinolinyl, naphthyl, or phenyl;

$R_8$ is hydrogen or $R_9$;
$R_8{'}$ is $R_8$ or fluorine;
$R_9$ is $C_{1-4}$ alkyl unsubstituted or substituted by one to three fluorines;
$R_{10}$ is $OR_8$ or $R_{11}$;
$R_{11}$ is hydrogen, or $C_{1-4}$ alkyl unsubstituted or substituted by one to three fluorines; or when $R_{10}$ and $R_{11}$ are as $NR_{10}R_{11}$ they may together with the nitrogen form a 5 to 7 membered ring comprised only of carbon atoms or carbon atoms and at least one heteroatom selected from O, N, or S;

$R_{13}$ is oxazolidinyl, oxazolyl, thiazolyl, pyrazolyl, triazolyl, tetrazolyl, irnidazolyl, imidazolidinyl, thiazolidinyl, isoxazolyl, oxadiazolyl, or thiadiazolyl, and each of these heterocyclic rings is connected through a carbon atom and each may be unsubstituted or substituted by one or two $C_{1-2}$ alkyl groups;

$R_{14}$ is hydrogen or $R_7$; or when $R_8$ and $R_{14}$ are as $NR_8R_{14}$ they may together with the nitrogen form a 5 to 7 membered ring comprised only of carbon atoms or carbon atoms and at least one heteroatom selected from O, N, or S; provided that:

$R_{15}$ is $C(O)R_{14}$, $C(O)NR_4R_{14}$, $S(O)_2R_7$, or $S(O)_2NR_4R_{14}$;

or a pharmaceutically acceptable salt thereof.

Another set of compounds of this invention are represented by Formula (II)

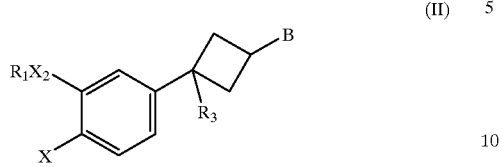

(II)

wherein:
R$_1$ is —(CR$_4$R$_5$)$_n$C(O)O(CR$_4$R$_5$)$_m$R$_6$, —(CR$_4$R$_5$)$_n$C(O)NR$_4$(CR$_4$R$_5$)$_m$R$_6$, —(CR$_4$R$_5$)$_n$O(CR$_4$R$_5$)$_m$R$_6$, or —(CR$_4$R$_5$)$_r$R$_6$ wherein the alkyl moieties may be unsubstituted or substituted with one or more fluorines;

m is 0 to 2;
n is 1 to 4;
r is 0 to 6;
R$_4$ and R$_5$ are independently hydrogen or C$_{1-2}$ alkyl;
R$_6$ is hydrogen, methyl, hydroxyl, aryl, halo substituted aryl, aryloxy C$_{1-3}$ alkyl, halo substituted aryloxy C$_{1-3}$ alkyl, indanyl, indenyl, C$_{7-11}$ polycycloalkyl, tetrahydrofuranyl, furanyl, tetrahydropyranyl, pyranyl, tetrahydrothienyl, thienyl, tetrahydrothiopyranyl, thiopyranyl, C$_{3-6}$ cycloalkyl, or a C$_{4-6}$ cycloalkyl containing one or two unsaturated bonds, wherein the cycloalkyl or heterocyclic moiety may be unsubstituted or substituted by 1 to 3 methyl groups, one ethyl group or an hydroxyl group;
provided that:
a) when R$_6$ is hydroxyl, then m is 2; or
b) when R$_6$ is hydroxyl, then r is 2 to 6; or
c) when R$_6$ is 2-tetrahydropyranyl, 2-tetrahydrothiopyranyl, 2-tetrahydrofuranyl, or 2-tetrahydrothienyl, then m is 1 or 2; or
d) when R$_6$ is 2-tetrahydropyranyl, 2-tetrahydrothiopyranyl, 2-tetrahydrofuranyl, or 2-tetrahydrothienyl, then r is 1 to 6;
e) when n is 1 and m is 0, then R$_6$ is other than H in —(CR$_4$R$_5$)$_n$O(CR$_4$R$_5$)$_m$R$_6$;
X is VR$_2$, halogen, nitro, NR$_4$R$_5$, or formyl amine;
V is O or S(O)$_{m'}$;
m' is 0, 1, or 2;
X$_2$ is O or NR$_8$;
R$_2$ is —CH$_3$ or —CH$_2$CH$_3$ unsubstituted or substituted by 1 or more fluorines;
R$_3$ is hydrogen, halogen, C$_{1-4}$ alkyl, halo-substituted C$_{1-4}$ alkyl, CH$_2$NHC(O)C(O)NH$_2$, —CH═CR$_{8'}$R$_{8'}$, cyclopropyl optionally substituted by R$_{8'}$, CN, OR$_8$, CH$_2$OR$_8$, NR$_8$R$_{10}$, CH$_2$NR$_8$R$_{10}$, C(Z)H, C(O)OR$_8$, C(O)NR$_8$R$_{10}$, or C≡CR$_8$.
Z is O, NR$_9$, NOR$_8$, NCN, C(—CN)$_2$, CR$_8$CN, CR$_8$NO$_2$, CR$_8$C(O)OR$_8$, CR$_8$C(O)NR$_8$R$_8$, C(—CN)NO$_2$, C(—CN)C(O)OR$_9$, C(—CN)C(O)NR$_8$R$_8$;
B is OR$_{14}$, OR$_{15}$, SR$_{14}$, S(O)$_m$R$_7$, S(O)$_2$NR$_{10}$R$_{14}$, NR$_{10}$R$_{14}$, NR$_{14}$C(O)R$_9$, NR$_{10}$C(Y')R$_{14}$, NR$_{10}$C(O)OR$_7$, NR$_{10}$C(Y')NR$_{10}$R$_{14}$, NR$_{10}$S(O)$_2$NR$_{10}$R$_{14}$, NR$_{10}$C(NCN)NR$_{10}$R$_{14}$, NR$_{10}$S(O)$_2$R$_7$, NR$_{10}$C(CR$_4$NO$_2$)NR$_{10}$R$_{14}$, NR$_{10}$C(NCN)SR$_9$, NR$_{10}$C(CR$_4$NO$_2$)SR$_9$, NR$_{10}$C(NR$_{10}$)NR$_{10}$R$_{14}$, NR$_{10}$C(O)C(O)NR$_{10}$R$_{14}$, or NR$_{10}$C(O)C(O)OR$_{14}$; or B is C(Y') R$_{14}$, C(O)OR$_{14}$, C(Y')NR$_{10}$R$_{14}$, C(NR$_{10}$)NR$_{10}$R$_{14}$, CN, C(NOR$_8$)R$_{14}$, C(NOR$_{14}$)R$_8$, C(NR$_8$)NR$_{10}$R$_{14}$, C(NR$_{14}$)NR$_8$R$_8$, C(NCN)NR$_{10}$R$_{14}$, C(NCN)SR$_{11}$, (2-, 4- or 5-imidazolyl), (3-, 4- or 5-pyrazolyl), (4- or 5-triazolyl[1,2,3]), (3- or 5-triazolyl[1,2,4]), (5-tetrazolyl), (2-, 4- or 5-oxazolyl), (3-, 4- or 5-isoxazolyl), (3- or 5-oxadiazolyl[1,2,4]), (2-oxadiazolyl[1,3,4]), (2-thiadiazolyl[1,3,4]), (2-,4- or 5-thiazolyl), (2-,4- or 5-oxazolidinyl), (2-, 4- or 5-thiadiazolinyl), or (2-, 4- or 5-imidazolidinyl), wherein all of the heterocyclic ring systems may be optionally substituted one or more times by R$_{14}$;
Y' is O or S;
R$_7$ is —(CR$_4$R$_5$)$_q$R$_{12}$ or C$_{1-6}$ alkyl wherein the R$_{12}$ or C$_{1-6}$ alkyl group is unsubstituted or substituted one or more times by methyl or ethyl unsubstituted or substituted by 1–3 fluorines, —F, —Br, —Cl, —NO$_2$, —NR$_{10}$R$_{11}$, —C(O)R$_8$, —CO$_2$R$_8$, —O(CH$_2$)$_q$R$_8$, —CN, —C(O)NR$_{10}$R$_{11}$, —O(CH$_2$)$_q$C(O)NR$_{10}$R$_{11}$, —O(CH$_2$)$_q$C(O)R$_8$, —NR$_{10}$C(O)NR$_{10}$R$_{11}$, —NR$_{10}$C(O)R$_{11}$, —NR$_{10}$C(O)OR$_9$, —NR$_{10}$C(O)R$_{13}$, —C(NR$_{10}$)NR$_{10}$R$_{11}$, —C(NCN)NR$_{10}$R$_{11}$, —C(NCN)SR$_9$, —NR$_{10}$C(NCN) SR$_9$, —NR$_{10}$C(NCN)NR$_{10}$R$_{11}$, —NR$_{10}$S(O)$_2$R$_9$, —S(O)$_m$R$_9$, —NR$_{10}$C(O)C(O)NR$_{10}$R$_{11}$, —NR$_{10}$C(O)C(O)R$_{10}$, or R$_{13}$;
q is 0, 1, or 2;
R$_{12}$ is R$_{13}$, C$_3$–C$_7$ cycloalkyl, (2-, 3- or 4-pyridyl), pyrimidyl, pyrazolyl, (1- or 2-midazolyl), pyrrolyl, piperazinyl, piperidinyl, morpholinyl, furanyl, (2- or 3-thienyl), uinolinyl, naphthyl, or phenyl;
R$_8$ is hydrogen or R$_9$;
R$_{8'}$ is R$_8$ or fluorine;
R$_9$ is C$_{1-4}$ alkyl unsubstituted or substituted by one to three fluorines;
R$_{10}$ is OR$_8$ or R$_{11}$;
R$_{11}$ is hydrogen, or C$_{1-4}$ alkyl unsubstituted or substituted by one to three fluorines; or when R$_{10}$ and R$_{11}$ are as NR$_{10}$R$_{11}$ they may together with the nitrogen form a 5 to 7 membered ring comprised only of carbon atoms or carbon atoms and at least one heteroatom selected from O, N, or S;
R$_{13}$ is oxazolidinyl, oxazolyl, thiazolyl, pyrazolyl, triazolyl, tetrazolyl, imidazolyl, imidazolidinyl, thiazolidinyl, isoxazolyl, oxadiazolyl, or thiadiazolyl, and each of these heterocyclic rings is connected through a carbon atom and each may be unsubstituted or substituted by one or two C$_{1-2}$ alkyl groups;
R$_{14}$ is hydrogen or R$_7$; or when R$_8$ and R$_{14}$ are as NR$_8$R$_{14}$ they may together with the nitrogen form a 5 to 7 membered ring comprised only of carbon atoms or carbon atoms and at least one heteroatom selected from O, N, or S; provided that:
R$_{15}$ is C(O)R$_{14}$, C(O)NR$_4$R$_{14}$, S(O)$_2$R$_7$, or S(O)$_2$NR$_4$R$_{14}$; provided that:
(f) When R$_{12}$ is N-pyrazolyl, N-imidazolyl, N-triazolyl, N-pyrrolyl, N-piperazinyl, or N-morpholinyl, then q is not 1;
or a pharmaceutically acceptable salt thereof.

This invention also relates to the pharmaceutical compositions comprising a compound of Formula (I) and/or (II) and a pharmaceutically acceptable carrier or diluent.

The invention also relates to a method of mediation or inhibition of the enzymatic activity (or catalytic activity) of PDE 4 in mammals, including humans, which comprises administering to a mammal in need thereof an effective amount of a compound of Formula (I) and (II) as shown below.

The invention further provides a method for the treatment of allergic and inflammatory disease which comprises administering to a mammal, including humans, in need thereof, an effective amount of a compound of Formula (I) and/or (II).

The invention also provides a method for the treatment of asthma which comprises administering to a mammal, including humans, in need thereof, an effective amount of a compound of Formula (I) and/or (II).

This invention also relates to a method of inhibiting TNF production in a mammal, including humans, which method comprises administering to a mammal in need of such treatment, an effective TNF inhibiting amount of a compound of Formula (I) and/or (II). This method may be used for the prophylactic treatment or prevention of certain TNF mediated disease states amenable thereto.

This invention also relates to a method of treating a human afflicted with a human immunodeficiency virus (HIV), which comprises administering to such human an effective TNF inhibiting amount of a compound of Formula (I) and/or (II).

Compounds of Formula (I) and/or (II) are also useful in the treatment of additional viral infections, where such viruses are sensitive to upregulation by TNF or will elicit TNF production in vivo.

In addition, compounds of Formula (I) and (II) are also useful in treating yeast and fungal infections, where such yeast and fungi are sensitive to upregulation by TNF or will elicit TNF production in vivo.

DETAILED DESCRIPTION OF THE INVENTION

Phosphodiesterase 4 inhibitors are useful in the treatment of a variety of allergic and inflammatory diseases including: asthma, chronic bronchitis, atopic dermatitis, urticaria, allergic rhinitis, allergic conjunctivitis, vernal conjunctivitis, eosinophilic granuloma, psoriasis, rheumatoid arthritis, septic shock, ulcerative colitis, Crohn's disease, reperfusion injury of the myocardium and brain, chronic glomerulonephritis, endotoxic shock and adult respiratory distress syndrome. In addition, PDE 4 inhibitors are useful in the treatment of diabetes insipidus and central nervous system disorders such as depression and multi-infarct dementia.

The viruses contemplated for treatment herein are those that produce TNF as a result of infection, or those which are sensitive to inhibition, such as by decreased replication, directly or indirectly, by the TNF inhibitors of Formula (I) and (II). Such viruses include, but are not limited to HIV-1, HIV-2 and HIV-3, cytomegalovirus (CMV), influenza, adenovirus and the Herpes group of viruses, such as, but not limited to, Herpes zoster and Herpes simplex.

This invention more specifically relates to a method of treating a mammal, afflicted with a human immunodeficiency virus (HIV), which comprises administering to such mammal an effective TNF inhibiting amount of a compound of Formula (I) and/or (II).

The compounds of this invention may also be used in association with the veterinary treatment of animals, other than in humans, in need of inhibition of TNF production. TNF mediated diseases for treatment, therapeutically or prophylactically, in animals include disease states such as those noted above, but in particular viral infections. Examples of such viruses include, but are not limited to feline immunodeficiency virus (FIV) or other retroviral infection such as equine infectious anemia virus, caprine arthritis virus, visna virus, maedi virus and other lentiviruses.

The compounds of this invention are also useful in treating yeast and fungal infections, where such yeast and fungi are sensitive to upregulation by TNF or will elicit TNF production in vivo. A preferred disease state for treatment is fungal meningitis. Additionally, the compounds of Formula (I) and/or (II) may be administered in conjunction with other drugs of choice for systemic yeast and fungal infections. Drugs of choice for fungal infections, include but are not limited to the class of compounds called the polymixins, such as Polymycin B, the class of compounds called the imidazoles, such as clotrimazole, econazole, miconazole, and ketoconazole; the class of compounds called the triazoles, such as fluconazole, and itranazole, and the class of compound called the Amphotericins, in particular Amphotericin B and liposomal Amphotericin B.

The compounds of Formula (I) and (II) may also be used for inhibiting and/or reducing the toxicity of an anti-fungal, anti-bacterial or anti-viral agent by administering an effective amount of a compound of Formula (I) and/or (II) to a mammal in need of such treatment. Preferably, a compound of Formula (I) and/or (II) is administered for inhibiting or reducing the toxicity of the Amphotericin class of compounds, in particular Amphotericin B.

The term "$C_{1-3}$ alkyl", "$C_{1-4}$ alkyl", "$C_{1-6}$ alkyl" or "alkyl" groups as used herein is meant to include both straight or branched chain radicals of 1 to 10, unless the chain length is limited thereto, including, but not limited to methyl, ethyl, n-propyl, isopropyl, n-butyl, sec-butyl, isobutyl, tert-butyl, and the like.

"Alkenyl" means both straight or branched chain radicals of 1 to 6 carbon lengths, unless the chain length is limited thereto, including but not limited to vinyl, 1-propenyl, 2-propenyl, or 3-methyl-2-propenyl.

The term "cycloalkyl" or "cycloalkyl alkyl" means groups of 3–7 carbon atoms, such as cyclopropyl, cyclopropylmethyl, cyclopentyl, or cyclohexyl.

"Aryl" or "aralkyl", unless specified otherwise, means an aromatic ring or ring system of 6–10 carbon atoms, such as phenyl, benzyl, phenethyl, or naphthyl. Preferably the aryl is monocyclic, i.e, phenyl. The alkyl chain is meant to include both straight or branched chain radicals of 1 to 4 carbon atoms. "Heteroaiyl" means an aromatic ring system containing one or more heteroatoms.

"Halo" means all halogens, i.e., chloro, fluoro, bromo, or iodo.

"Inhibiting the production of IL-1" or "inhibiting the production of TNF" means:

a) a decrease of excessive in vivo IL-1 or TNF levels, respectively, in a human to normal levels or below normal levels by inhibition of the in vivo release of IL-1 by all cells, including but not limited to monocytes or macrophages;

b) a down regulation, at the translational or transcriptional level, of excessive in vivo IL-1 or TNF levels, respectively, in a human to normal levels or below normal levels; or c) a down regulation, by inhibition of the direct synthesis of IL-1 or TNF levels as a postranslational event.

The phrase "TNF mediated disease or disease states" means any and all disease states in which TNF plays a role, either by production of TNF itself, or by TNF causing another cytokine to be released, such as but not limited to IL-1 or IL-6. A disease state in which IL-1, for instance is a major component, and whose production or action, is exacerbated or secreted in response to TNF, would therefore be considered a disease state mediated by TNF. As TNF-β (also known as lymphotoxin) has close structural homology with TNF-α (also known as cachectin), and since each induces similar biologic responses and binds to the same cellular receptor, both TNF-α and TNF-β are inhibited by the compounds of the present invention and thus are herein referred to collectively as "TNF" unless specifically delineated otherwise. Preferably TNF-α is inhibited.

"Cytokine" means any secreted polypeptide that affects the functions of cells, and is a molecule which modulates interactions between cells in immune, inflammatory, or hematopoietic responses. A cytokine includes, but is not limited to, monokines and lymphokines regardless of which cells produce them. The cytokine inhibited by the present invention for use in the treatment of a HIV-infected human must be a cytokine which is implicated in (a) the initiation and/or maintenance of T cell activation and/or activated T cell-mediated HIV gene expression and/or replication, and/or (b) any cytokine-mediated disease associated problem such as cachexia or muscle degeneration. Preferrably, his cytokine is TNF-α.

All of the compounds of Formula (I) and (II) are useful in the method of inhibiting the production of TNF, preferably by macrophages, monocytes or macrophages and monocytes, in a mammal, including humans, in need thereof. All of the compounds of Formula (I) and (II) are useful in the method of inhibiting or mediating the enzymatic or catalytic activity of PDE 4 and in treatment of disease states mediated thereby.

Preferred compounds are as follows:

When $R_1$ for the compounds of Formula (I) and (II) is an alkyl substituted by 1 or more halogens, the halogens are preferably fluorine and chlorine, more preferably a $C_{1-4}$ alkyl substituted by 1 or more fluorines. The preferred halo-substituted alkyl chain length is one or two carbons, and most preferred are the moieties —$CF_3$, —$CH_2F$, —$CHF_2$, —$CF_2CHF_2$, —$CH_2CF_3$, and —$CH_2CHF_2$. Preferred $R_1$ substitutents for the compounds of Formula (I) and (II) are $CH_2$-cyclopropyl, $CH_2$-$C_{5-6}$ cycloalkyl, $C_{4-6}$ cycloalkyl unsubstituted or substituted with OH, $C_{7-11}$ polycycloalkyl, (3- or 4-cyclopentenyl), phenyl, tetrahydrofuran-3-yl, benzyl or $C_{1-2}$ alkyl unsubstituted or substituted by 1 or more fluorines, —$(CH_2)_{1-3}C(O)O(CH_2)_{0-2}CH_3$, —$(CH_2)_{1-3}O(CH_2)_{0-2}CH_3$, and —$(CH_2)_{2-4}OH$.

When the $R_1$ term is $(CR_4R_5)$, the $R_4$ and $R_5$ terms are independently hydrogen or alkyl. This allows for branching of the individual methylene units as $(CR_4R_5)_n$ or $(CR_4R_5)_m$; each repeating methylene unit is independent of the other, e.g., $(CR_4R_5)_n$ wherein n is 2 can be —$CH_2CH(-CH_3)$—, for instance. The individual hydrogen atoms of the repeating methylene unit or the branching hydrocarbon can be unsubstituted or be substituted by fluorine independent of each other to yield, for instance, the preferred $R_1$ substitutions, as noted above.

When $R_1$ is a $C_{7-11}$ polycycloalkyl, examples are bicyclo[2.2.1]-heptyl, bicyclo[2.2.2]octyl, bicyclo[3.2.1]octyl, tricyclo[5.2.1.0$^{2,6}$]decyl, etc. additional examples of which are described in Saccamano et al., WO 87/06576, published Nov. 5, 1987, whose disclosure is incorporated herein by reference in its entirety.

Preferred A terms are O, NCN, $NR_7$, $NOR_{14}$, $NOR_{15}$, $NNR_4R_{14}$, $NNR_4R_{15}$, 2-(1,3-dithiane), dimethylthio ketal, 2-(1,3-dioxolane), or dimethyl ketal. More preferred are O, $NR_7$, $NOR_{14}$, $NOR_{15}$, and 2-(3-dioxolane).

Preferred X groups for Formula (I) and (II) are those wherein X is $VR_2$ and V is oxygen. The preferred $X_2$ group for Formula (I) and (II) is that wherein $X_2$ is oxygen. The preferred $X_3$ group for Formula (I) and (II) is that wherein $X_3$ is hydrogen. Preferred $R_2$ groups, where applicable, is a $C_{1-2}$ alkyl unsubstituted or substituted by 1 or more halogens. The halogen atoms are preferably fluorine and chlorine, more preferably fluorine. More preferred $R_2$ groups are those wherein $R_2$ is methyl, or the fluoro-substituted alkyls, specifically a $C_{1-2}$ alkyl, such as a —$CF_3$, —$CHF_2$, or —$CH_2CHF_2$ moiety. Most preferred are the —$CHF_2$ and —$CH_3$ moieties.

Preferred $R_7$ moieties include $R_{13}$, unsubstituted or substituted —$(CH_2)_{0-2}$(2-, 3- or 4-pyridyl), $(CH_2)_{1-2}$(2-imidazolyl), $(CH_2)_2$(4-morpholinyl), $(CH_2)_2$(4-piperazinyl), $(CH_2)_{1-2}$(2-thienyl), $(CH_2)_{1-2}$(4-thiazolyl), unsubstituted or substituted pyrimidinyl, and substituted or unsubstituted $(CH_2)_{0-2}$phenyl.

Preferred rings when $R_{10}$ and $R_{11}$ in the moiety —$NR_{10}R_{11}$ together with the nitrogen to which they are attached form a 5 to 7 membered ring comprised only of carbon atoms or carbon atoms and at least one heteroatom selected from O, N, or S include, but are not limited to 1-imidazolyl, 2-($R_8$)-1-imidazolyl, 1-pyrazolyl, 3-($R_8$)-1-pyrazolyl, 1-triazolyl, 2-triazolyl, 5-($R_8$)-1-triazolyl, 5-($R_8$)-2-triazolyl, 5-($R_8$)-1-tetrazolyl, 5-($R_8$)-2-tetrazolyl, 1-tetrazolyl, 2-tetrazloyl, morpholinyl, piperazinyl, 4-($R_8$)-1-piperazinyl, or pyrrolyl ring.

Preferred rings when $R_8$ and $R_{14}$ in the moiety —$NR_8R_{14}$ together with the nitrogen to which they are attached may form a 5 to 7 membered ring comprised only of carbon atoms or carbon atoms and at least one heteroatom selected from O, N, or S include, but are not limited to 1-imidazolyl, 1-pyrazolyl, 1-triazolyl, 2-triazolyl, 1-tetrazolyl, 2-tetrazolyl, morpholinyl, piperazinyl, and pyrrolyl. The respective rings may be additionally substituted, where applicable, on an available nitrogen or carbon by the moiety $R_7$ as described herein for Formula (I) and (II). Illustrations of such carbon substitutions includes, but is not limited to, 2-($R_7$)-1-imidazolyl, 4-($R_7$)-1-imidazolyl, 5-($R_7$)-1-imidazolyl, 3-($R_7$)-4-($R_7$)-1-pyrazolyl, 5-($R_7$)-1-pyrazolyl, 4-($R_7$)-2-triazolyl, 5-($R_7$)-2-triazolyl, 4-($R_7$)-1-triazolyl, 5-($R_7$)-1-triazolyl, 5-($R_7$)-1-tetrazolyl, and 5-($R_7$)-2-tetrazolyl. Applicable nitrogen substitution by $R_7$ includes, but is not limited to, 1-($R_7$)-2-tetrazolyl, 2-($R_7$)-1-tetrazolyl, 4-($R_7$)-1-piperazinyl. Where applicable, the ring may be substituted one or more times by $R_7$.

Preferred groups for $NR_8R_{14}$ which contain a heterocyclic ring are 5-($R_{14}$)-1-tetrazolyl, 2-($R_{14}$)-1-imidazolyl, 5-($R_{14}$)-2-tetrazolyl, 4-($R_{14}$)-1-piperazinyl, or 4-($R_{15}$)-1-piperazinyl.

Preferred rings for $R_{13}$ include (2-, 4- or 5-imidazolyl), (3-, 4- or 5-pyrazolyl), (4- or 5-triazolyl[1,2,3]), (3- or 5-triazolyl[1,2,4]), (5-tetrazolyl), (2-, 4- or 5-oxazolyl), (3-, 4- or 5-isoxazolyl), (3- or 5-oxadiazolyl[1,2,4]), (2-oxadiazolyl[1,3,4]), (2-thiadiazolyl[1,3,4]), (2-, 4-, or 5-thiazolyl), (2-, 4-, 5-oxazolidityl), (2-, 4-, or 5-thiazolidinyl), or (2-, 4-, or 5-imidazolidinyl).

When the $R_7$ group is unsubstituted or substituted by a heterocyclic ring such as imidazolyl, pyrazolyl, pyrimidinyl, triazolyl, tetrazolyl, or thiazolyl, the heterocyclic ring itself may be unsubstituted or substituted by $R_8$ either on an available nitrogen or carbon atom, such as 1-($R_8$)-2-imidazolyl, 1-($R_8$)-4-imidazolyl, 1-($R_8$)-5-imnidazolyl, 1-($R_8$)-3-pyrazolyl, 1-($R_8$)-4-pyrazolyl, 1-($R_8$)-5-pyrazolyl, 1-($R_8$)-4-triazolyl, or 1-($R_8$)-5-triazolyl. Where applicable, the ring may be substituted one or more times by $R_8$.

$R_3$ is preferably —CH≡$CR_8$·$R_8$·CN, or CδCR$_8$ in both Formula (I) and Formula (II) compounds.

Preferred are those compounds of Formula (I) wherein $R_1$ is —$CH_2$-cyclopropyl, —$CH_2$-$C_{5-6}$ cycloalkyl, —$C_{4-6}$ cycloalkyl unsubstituted or substituted with OH, tetrahydrofuran-3-yl, (3- or 4-cyclopentenyl), benzyl or —$C_{1-2}$ alkyl unsubstituted or substituted by 1 or more fluorines, and —$(CH_2)_{2-4}OH$; $R_2$ is methyl or fluoro-substituted alkyl, $R_3$ is C≡$CR_8$ or CN, X is $VR_2$, and A is O, $NR_7$.

As regards preferred compounds of Formula (II) they are those wherein $R_1$ is —$CH_2$-cyclopropyl, —$CH_2$—$C_{5-6}$ cycloalkyl, —$C_{4-6}$ cycloalkyl unsubstituted or substituted with OH, tetrahydrofuran-3-yl, (3- or 4-cyclopentenyl), benzyl or —$C_{1-2}$ alkyl unsubstituted or substituted by 1 or more fluorines, and —$(CH_2)_{2-4}$ OH; $R_2$ is methyl or fluoro-substituted alkyl, $R_3$ is CN, X is $VR_2$; and B is $OR_{14}$, $OR_{15}$, $C(O)OR_{14}$ or $NR_{10}R_{14}$.

Most preferred are those compounds of Formula (I) are those wherein $R_1$ is —$CH_2$-cyclopropyl, cyclopentyl, 3-hydroxycyclopentyl, methyl or $CF_2H$; X is $VR_2$; V is oxygen; $X_2$ is oxygen; $R_2$ is $CF_2H$ or methyl; $R_3$ is CN; and A is O or $NR_7$.

As regards the most preferred compounds of Formula (II), they are the same as for those of Formula (I) where Formula (II) shares a group in common with Formula (I). As regards the B group in Formula (II), the preferred embodiment where B is $OR_{14}$, $OR_{15}$, $C(O)OR_{14}$ or $NR_{10}R_{14}$ Pharmaceutically acceptable salts of the instant compounds, where they can be prepared, are also intended to be covered by this invention. These salts will be ones which are acceptable in their application to a pharmaceutical use. By that it is meant that the salt will retain the biological activity of the parent compound and the salt will not have untoward or deleterious effects in its application and use in treating diseases.

Pharmaceutically acceptable salts are prepared in a standard manner. If the parent compound is a base it is treated with an excess of an organic or inorganic acid in a suitable solvent. If the parent compound is an acid, it is treated with an inorganic or organic base in a suitable solvent.

Pharmaceutical compositions of the present invention comprise a pharmaceutical carrier or diluent and some amount of a compound of the Formula (I) and (II). The compound may be present in an amount to effect a physiological response, or it may be present in a lesser amount such that the user will need to take two or more units of the composition to effect the treatment intended. These compositions may be made up as a solid, liquid or in a gaseous form. Or one of these three forms may be transformed to another at the time of being administered such as when a solid is delivered by aerosol means, or when a liquid is delivered as a spray or aerosol.

The nature of the composition and the pharmaceutical carrier or diluent will, of course, depend upon the intended route of administration, for example parenterally, topically, orally or by inhalation.

For topical administration the pharmaceutical composition will be in the form of a cream, ointment, liniment, lotion, pastes, aerosols, and drops suitable for administration to the skin, eye, ear, or nose.

For parenteral administration the pharmaceutical composition will be in the form of a sterile injectable liquid such as an ampule or an aqueous or non-aqueous liquid suspension.

For oral administration the pharmaceutical composition will be in the form of a tablet, capsule, powder, pellet, atroche, lozenge, syrup, liquid, or emulsion.

When the pharmaceutical composition is employed in the form of a solution or suspension, examples of appropriate pharmaceutical carriers or diluents include: for aqueous systems, water; for non-aqueous systems, ethanol, glycerin, propylene glycol, corn oil, cottonseed oil, peanut oil, sesame oil, liquid parafins and mixtures thereof with water; for solid systems, lactose, kaolin and mannitol; and for aerosol systems, dichlorodifluoromethane, chlorotrifluoroethane and compressed carbon dioxide. Also, in addition to the pharmaceutical carrier or diluent, the instant compositions may include other ingredients such as stabilizers, antioxidants, preservatives, lubricants, suspending agents, viscosity modifiers and the like, provided that the additional ingredients do not have a detrimental effect on the therapeutic action of the instant compositions.

The pharmaceutical preparations thus described are made following the conventional techniques of the pharmaceutical chemist as appropriate to the desired end product.

In these compositions, the amount of carrier or diluent will vary but preferably will be the major proportion of a suspension or solution of the active ingredient. When the diluent is a solid it may be present in lesser, equal or greater amounts than the solid active ingredient.

Usually a compound of formula I is administered to a subject in a composition comprising a nontoxic amount sufficient to produce an inhibition of the symptoms of a disease in which leukotrienes are a factor. Topical formulations will contain between about 0.01 to 5.0% by weight of the active ingredient and will be applied as required as a preventative or curative agent to the affected area. When employed as an oral, or other ingested or injected regimen, the dosage of the composition is selected from the range of from 50 mg to 1000 mg of active ingredient for each administration. For convenience, equal doses will be administered 1 to 5 times daily with the daily dosage regimen being selected from about 50 mg to about 5000 mg.

It will be recognized that some of the compounds of Formula (I) and (II) may exist in both racemic and optically active forms; some may also exist in distinct diastereomeric forms possessing distinct physical and biological properties. All of these compounds are considered to be within the scope of the present invention.

The following examples are given to further illustrate the described invention. These examples are intented solely for illustrating the invention and should not be read to limit the invention in any manner. Reference is made to the claims for what is reserved to the inventors hereunder.

No unacceptable toxicological effects are expected when these compounds are administered in accordance with the present invention.

METHODS OF PREPARATION

Synthetic Scheme(s) With Textual Description

Cyclobutanol 2-Scheme 1 may be prepared from the benzyl nitrile 1-Scheme 1, which was itself prepared as described in U.S. Pat. No. 5,631,286, by first treating with a suitable base, such as an alkyllithium, especially methyllithium, in a suitable solvent, such as ether or tetrahydrofuran, followed by anion quench with epibromohydrin to obtain the epoxymethyl adduct by the method of Corkel and Durst. This intermediate may be isolated or preferably treated in situ with a suitable reagent, such as methylmagnesium iodide, to induce rearrangement to cyclobutanol 2-Scheme 1 Corkel et al., *Can. J. Chetm.*; 56: 505–511, 1978, Decesare, et al., *Can. J. Chem.*; 59: 1415–1424, 1981, Corkel et al. *J. Org. Chem.*; 41: 3648–3650, 1976. Oxidation to cyclobutanone 3-Scheme 1 may be achieved by use of a suitable oxidizing reagent, especially a chromium complex, especially pyridinium chlorochromate, in a suitable solvent, such as dichloromethane. Cyclobutanone 3-Scheme 1 may be reduced by one of many possible reducing agents, for example a borohydride, in this example lithium borohydride, in a suitable solvent, such as ethanol, tetrahydrofuran or dimethoxyethane, at temperatures from −78° C. to room temperature. The relative ratio of cis to trans isomers of the cyclobutanol 2-Scheme 1 is partially determined by the reducing reagent, solvent and reaction temperature chosen. Separation of the isomers may be achieved by preparation of a derivative, for example, a benzoate derivative, especially the 3-bromobenzoates 4a- and 4b-Scheme 1 by treatment of the isomer mixture with the appropriate benzoyl chloride, and a suitable base, such as triethylamine, in a suitable solvent, such as dichloromethane, followed by silica gel separation. Separated cis and trans cyclobutanols 2a- and 2b-Scheme 1 may be obtained by hydrolysis of each separate isomer of 3-bromobenzoates 4a- or 4b-Scheme 1, for example with sodium hydroxide in an aqueous solvent, such as methanol.

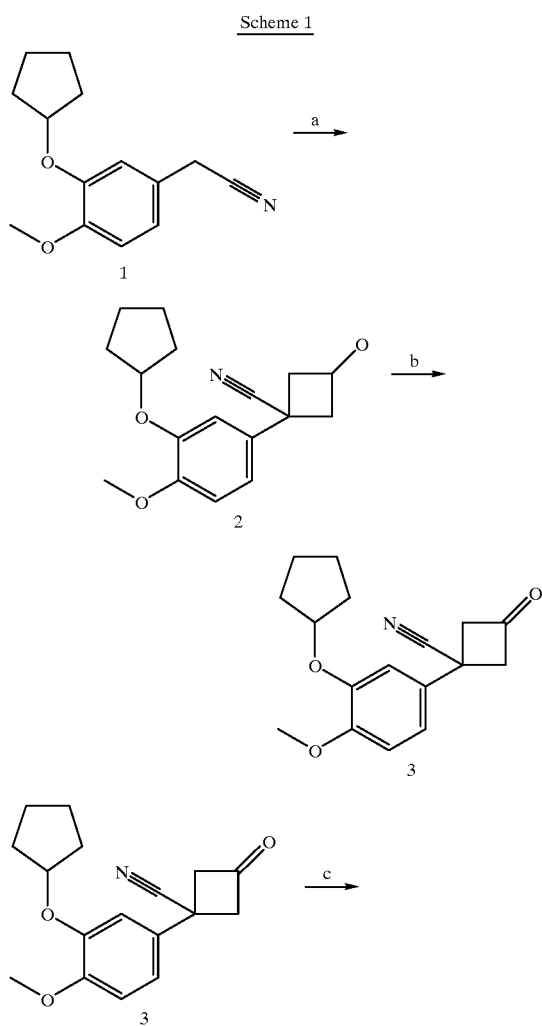

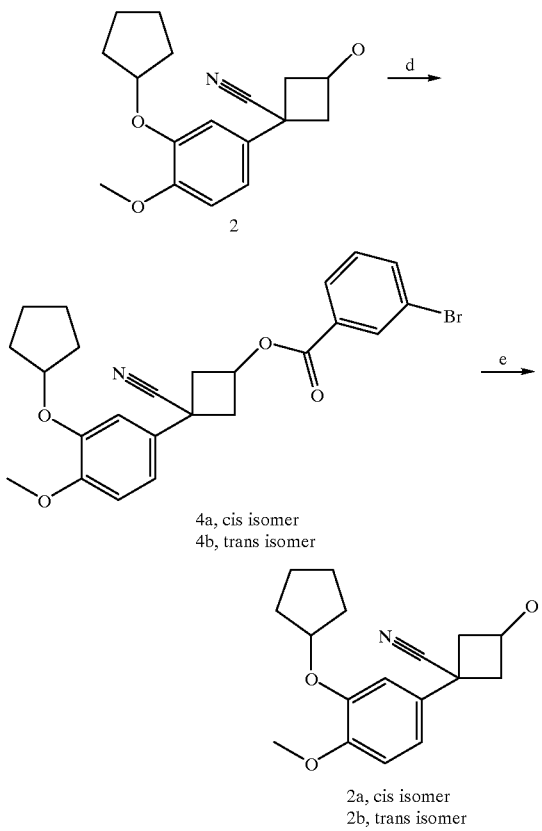

Reagents: a) i. MeLi/Et$_2$O, THF, −78° C., ii. bromoopihydrin, RT, iii. MeMgI/Et$_2$O, −78° C. to RT; b) PCC, CH$_2$Cl$_2$; c) LiBH$_4$, THF, −78° C.; d) 3-bromobenzoyl chloride, Et$_3$N, DMAP, CH$_2$Cl$_2$; e) NaOH, H$_2$O, MeOH.

The cyciobutanol isomers 1 a- and 1 b-Scheme 2 may be separately elaborated to the opposite amine isomers 2a- and 2b-Scheme 2 , by first subjecting them to Mitsunobu reaction conditions, such as diethyl azodicarboxylate, triphenylphosphine and phthalimide, in a suitable solvent, such as tetrahydrofuran, followed by cleavage of the intermediate phthalimide with a suitable reagent, such as hydrazine, in a suitable solvent, such as a mixture of ethanol and tetrahydrofuran. [Mitsunobu, Synth, 1, 1981]

Scheme 2

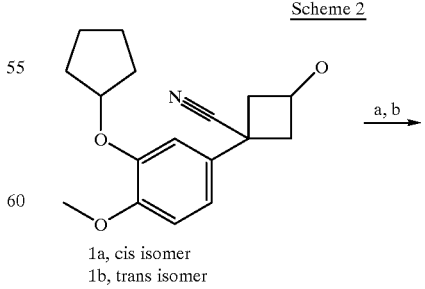

-continued

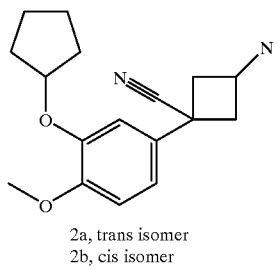

2a, trans isomer
2b, cis isomer

Reagents: a) DEAD, PPh₃, phthalimide, THF; b) N₂H₄H₂O, EtOH, THF.

Cyanocyclobutanone 1-Scheme 3 may be protected, for example as a ketal, by treatment under suitable reaction conditions, for example with 1,2-bis(trimethylsilyloxy) ethane and catalytic trimethylsilyl trifluoromethanesulfonate in a suitable solvent, such as dichloromethane. The nitrile group may then be reduced to the alchol by treatment with suitable reducing reagents, such as diisobutylaluminum hydride, in a suitable solvent, such as toluene or a mixture ethers, such as tetrahydrofuran and tetrabutyl methyl ether, followed by a borohydride, such as sodium borohydride, in a suitable solvent, such as an alcohol, or an ether, such as dimethoxyethane or tetrahydrofuran at a temperature from −78° C. to room temperature, preferably at 0° C. This ketal may then be deprotected by treatment with an acidic reagent, such as hydrogen chloride or p-toluenesulfonic acid, in a suitable solvent, such as aqueous tetrahydrofuran, at elevated temperatures, such as 65° C. The alcohol may then be protected, for example as an acetate, by treatment with suitable reagents, such as acetic anhydride, in the presence of a base, such as pyridine, in a suitable solvent, such as dichloromethane, at room temperature to refluxing temperatures, preferably 35° C., to provide cyclobutanone 2-Scheme 3.

Cyclobutanone 2-Scheme 3 may be homologated to the carboxylic ester 4-Scheme 3, for example by formation of a ketene thioacetal 3-Scheme 3, by treatment with 2-lithio-2-trimethylsilyl-1,3-dithiane, prepared with an alkyllithium, especially ii-butyllithium, in a suitable solvent, such as tetrahydrofuran, at −78° C. to room temperature, preferably at 0° C. [Carey et al, *J. Org. Chem.*, 37: 1926, 1972]. Ketene thioacetal 3-Scheme 3 may be hydrolyzed by suitable reagents, such as trifluoroacetic acid, in a suitable solvent, such as acetonitrile and water, at elevated temperature, such as 60° C., then hydrogen peroxide, then esterification by one of various methods, such as with an alcohol, such as methanol, and an acidic reagent, such as trimethylsilyl chloride or hydrogen chloride, or with diazomethane in ether. The preferred hydrolysis method is treatment with a mercury salt, such as mercury(II) chloride, and an acid, such as perchloric acid, in an alcoholic solvent, such as methanol, at elevated temperature, preferably at reflux.

Alcohol mixture 4-Scheme 3 may be oxidized to the the aldehydes 5a- and 5b-Scheme 3 by various methods, for example with a chromium reagent, such as pyridinium chlorochromate, in a suitable solvent, such as dichloromethane. Separation of the cis and trans isomers can conveniently be carried out at this point. Aldehyde 5a- or 5b-Scheme 3 may be condensed with an amine-delivering reagent, such as hydroxylamine hydrochloride, [Saidna et al, *Synth*, 190, 1982] in the presence of a base, such as pyridine, in a suitable solvent, such as toluene at refluxing temperature, preferably with removal of water from the reaction. The resulting hydroxylimine 6a- or 6b-Scheme 3 may be dehydrated to the nitrile with a variety of reagents, [Carotti, *Synth*, 56, 1979] such as trifluoromethanesulfonic anhydride, in the presence of a base, such as triethylamine, in a suitable solvent, such as dichloromethane. Ester 7a- or 7b-Scheme 3 may be saponified to the cyclobutanecarboxylic acid 8a- or 8b-Scheme 3 by a number of methods, such as treatment with potassium hydroxide in a mixture of tetrahydrofuran, methanol and water.

Scheme 3

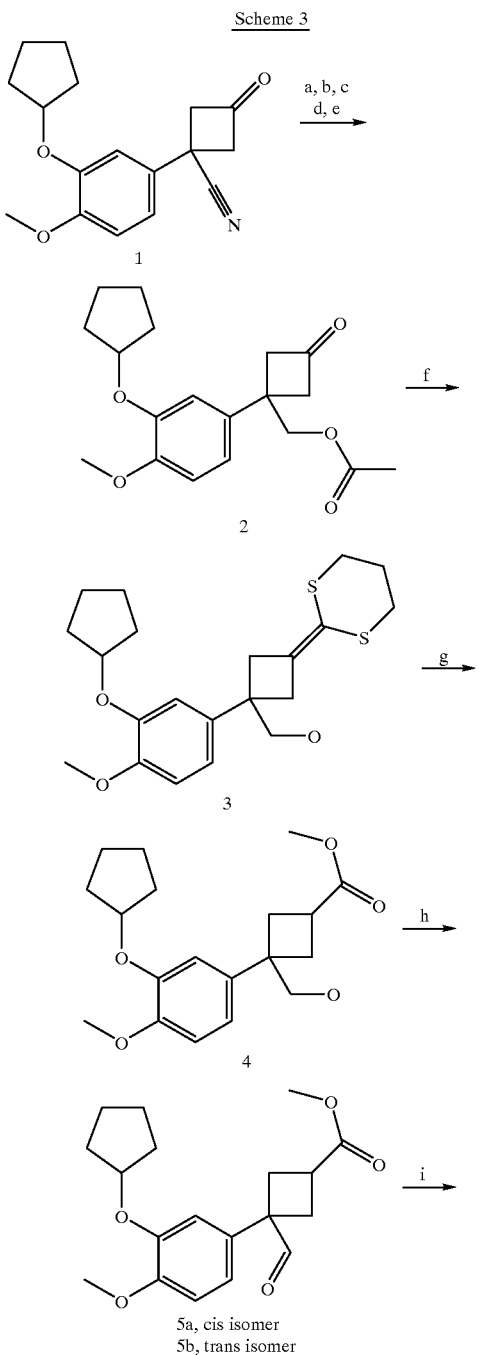

5a, cis isomer
5b, trans isomer

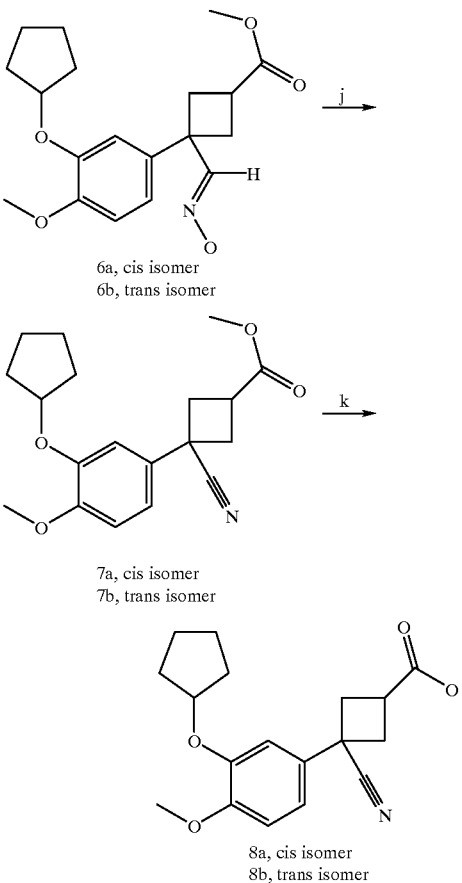

6a, cis isomer
6b, trans isomer 7a, cis isomer
7b, trans isomer 8a, cis isomer
8b, trans isomer Reagents: a) TMSOCH$_2$CH$_2$OTMS, TMSOTf, CH$_2$Cl$_2$, −78° C. to RT; b) DIBAL-H, THF, TBME, −15° C.; c) NaBH$_4$, DME, 0° C.; d) HCl, H$_2$O, THF, 60° C.; e) Ac$_2$O, pyridine, CH$_2$Cl$_2$, 35° C.; f) 2-TMS-1,3-dithiane, n-BuLi/hexanes, THF, 0° C.; g) HClO$_4$, HgCl$_2$, MeOH, 65° C.; h) PCC, CH$_2$Cl$_2$; i) NH$_2$OH.HCl, pyridine, toluene, 4 A sieves, 110° C.; j) Tf$_2$O, Et$_3$N, CH$_2$Cl$_2$; k) i. KOH, THF, MeOH, H$_2$O; ii. HCl, H$_2$O.

SYNTHETIC EXAMPLES

Example 1

3-Cyano-3-(3-cyclopentyloxy-4-methoxyphenyl) cyclobutan-1-one 1a 3-Cyano-3-(3-cyclopentyloxy-4-methoxyphenyl) cyclobutan-1-ol.

A solution of (3-cyclopentyloxy-4-methoxyphenyl) acetonitrile (prepared as described in U.S. Pat. No. 5,631,284) (12.65 g, 54.7 mmol) in tetrahydrofuran (400 mL) and examethylphosphoramide (16 mL) at −78° C. under an argon atmosphere was first treated dropwise over 75 min with 1.4 M methyllithium in diethyl ether (47 mL, 65.6 mmol), then with epibromohydrin (5.6 mL, 65.6 mmol). The reaction was allowed to warm to room temperature and was stirred for 3 h, then was recooled to −78° C. and was treated dropwise over 0.5 h with 3.0 M methylmagnesium iodide in diethyl ether. The reaction was stirred at room temperature for 20 h, diluted with aqueous ammonium chloride and water, and was extracted three times with tertbutyl methyl ether. The organic extract was dried (magnesium sulfate), was evaporated and was partially purified by flash chromatography, eluting with 35:65 ethyl acetate:hexanes to provide a mixture of cis- and trans-3-cyano-3-(3-cyclopentyloxy-4-methoxyphenyl)cyclobutan-1-ol and cis- and trans-2-cyano-2-(3-cyclopentyloxy-4-methoxyphenyl)-1-cyclopropylmethanol (~9: 1, by $^1$H-NMR) as a dark orange oil (10.01 g, 64%).

1b 3-Cyano-3-(3-cyclopentyloxy-4-methoxyphenyl) cyclobutan-1-one.

A solution of 3-cyano-3-(3-cyclopentyloxy-4-methoxyphenyl)cyclobutan-1-ol mixture (0.67 g, 2.32 mmol) in dichloromethane (5 mL) was rapidly added to a suspension of pyridinium chlorochromate (0.75 g, 3.48 mmol) in dichloromethane (10 mL) at room temperature under an argon atmosphere. The reaction was stirred for 4 h, was diluted with diethyl ether (30 mL), was stirred for 0.5 h, was filtered through Celite and was evaporated. Purification by flash chromatography, eluting with 2:8 ethyl acetate:hexanes provided product as a waxy white solid (0.38 g, 58%): m.p. 68–69° C.

Analysis Calcd for $C_{17}H_{19}NO_3 \cdot 0.125 H_2O$: C 71.00, H 6.74, N 4.87; found C 71.08, H 6.70, N 4.75.

Example 2 cis-3—Cyano-3-(3-cyclopentyloxy-4-methoxyphenyl)cyclobutan-1-ol 2a 3-Cyano-3-(3-cyclopentyloxy-4-methoxyphenyl) cyclobutan-1-ol To a solution of 3-cyano-3-(3-cyclopentyloxy-4-methoxyphenyl)cyclobutan-1-one (8.63 g, 30.3 mmol) in tetrahydrofuran (200 mL) at −78° C. under an argon atmosphere was added over 75 min a slurry of lithium borohydride (1.98 g, 90.8 mmol) in tetrahydrofuran (200 mL). The reaction was stirred for 0.5 h, and was carefully poured into a 0° C. saturated solution of ammonium chloride. 10% Hydrochloric acid was used to adjust to pH 3–4, the mixture was warmed to room temperature, was diluted with water and was extracted with three portions of tert butyl methyl ether. The organic extract was dried (magnesium sulfate) and evaporated to provide crude product (8.96 g, 100%) as a pale green oil. $^1$H-NMR shows an isomer ratio of ~3:1 cis:trans.

2b 1-[cis-3-Cyano-3-(3-cyclopentyloxy-4-methoxyphenyl) cyclobutyl]-3-bromobenzoate and 1-[trans-3-cyano-3-(3-cyclopentyloxy-4-methoxyphenyl)cyclobutyl]-3-bromobenzoate.

To a solution of 3-cyano-3-(3-cyclopentyloxy-4-methoxyphenyl)cyclobutan-1-ol (2.06 g, 7.17 mmol) in dichloromethane (50 mL) at room temperature under an argon atmosphere were added dimethylaminopyridine (0.09 g, 0.72 mmol), triethylamine (1.50 mL, 10.8 mmol), and 3-bromobenzoyl chloride (1.05 mL, 7.89 mmol). The reaction was stirred for 24 h, was diluted with water, and was extracted with three portions of dichloromethane. The organic extact was dried (magnesium sulfate) and evaporated. Purification required several chromatographies, eluting with 5–7% ethyl acetate in hexanes, to provide both products: 1-[cis-3Cyano-3-(3-cyclopentyloxy-4-methoxyphenyl)cyclobutyl]-3-bromobenzoate was isolated as a waxy white solid (1.30 g, 39%), m.p.82–83° C., R$_f$=0.34 (2:8 ethyl acetate:hexanes), and 1-[trans-3-cyano-3-(3-cyclopentyloxy-4-methoxyphenyl)cyclobutyl]-3-bromobenzoate was isolated as a colorless oil, which solidified to a waxy white solid (0.46 g, 14%), m.p.88–89° C., R$_f$=0.37 (2:8 ethyl acetate:hexanes). Additional product was isolated as a mixture of isomers (0.41 g, 12%).

2c cis-3-Cyano-3-(3-cyclopentyloxy-4-methoxyphenyl) cyclobutan-1-ol.

1-[cis-3-Cyano-3-(3-cyclopentyloxy-4-methoxyphenyl) cyclobutyl]-3-bromobenzoate (2.77 g, 5.94 mmol) was dissolved in a solution of sodium hydroxide (0.81 g, 20 mmol) in methanol (230 mL) and the reaction was stirred for 0.5 h at room temperature under an argon atmosphere. The reaction was diluted with water, methanol was evaporated off and the residue was extracted with three portions of dichloromethane. The organic extract was dried (magnesium sulfate) and evaporated. Purification by flash chromatography, eluting with 35:65 ethyl acetate:hexanes provided product as a waxy white solid (1.568 g, 92%), m.p. 53–55° C.

Analysis Calcd for $C_{17}H_{21}NO_3$: C 71.06, H 7.37, N 4.87; found C 70.80, H 7.30, N 4.78.

NOe experiments confirmed the relative stereochemistry to be cis.

Example 3 trans-3-Cyano-3-(3-cyclopentyloxy-4-methoxyphenyl)cyclobutan-1-ol

1-[trans-3-Cyano-3-(3-cyclopentyloxy-4-methoxyphenyl)cyclobutyl]-3-bromobenzoate (from example 5b) (0.46 g, 0.98 mmol) was dissolved in a solution of sodium hydroxide (0.13 g, 3.35 mmol) in methanol (38 mL) and the reaction was stirred for 0.5 h at room temperature under an argon atmosphere. The reaction was diluted with water, methanol was evaporated off and the residue was extracted with three portions of dichloromethane. The organic extract was dried (magnesium sulfate) and evaporated Purification by flash chromatography, eluting with 3:7 ethyl acetate:hexanes provided product as a white solid (0.23 g, 82%), m.p.97–98° C.

Analysis Calcd for $C_{17}H_{21}NO_3.0.25 H_2O$: C 69.96, H 7.43, N 4.80; found C 70.26, H 7.34, N 5.10.

NOe experiments confirmed the relative stereochemistry to be trans.

Example 4 trans-1-Amino-3-cyano-3-(3-cyclopentyloxy-4-methoxyphenyl)cyclobutane

A solution of cis-3-cyano-3-(3-cyclopentyloxy-4-methoxyphenyl)cyclobutan-1-ol (0.25 g, 0.87 mmol) in tetrahydrofuran (10 mL) was treated with phthalimide (0.19 g, 1.31 mmol), triphenylphosphinc (0.34 g, 1.31 mmol) and dropwise with diethyl azodicarboxylate (0,21 mL, 1.31 mmol). The reaction was stirred at room temperature under an argon atmosphere for 20 h, was evaporated and was partially purified by flash chromatography, eluting with 2:8 ethyl acetate : hexanes to provide a mixture of trans-3-Cyano-3-(3-cyclopentyloxy-4-methoxyphenyl)-1-phthalimidocyclobutane:phthalimide (~1:1) as a white solid (0.18 g). This intermediate mixture was dissolved in ethanol (2 mL) and tetrahydrofuran (1 mL), was treated with hydrazine monohydrate (0.23 mL, 4.4 mmol) and was stirred at room temperature under an argon atmosphere for 18 h. The reaction was diluted with water and was extracted with three portions of 1:9 methanol:dichloromethane. The organic extract was dried (magnesium sulfate) and evaporated. Purification by two flash chromatographies, eluting with 1:99 methanol:dichloromethane provided product as ayellow oil (0.06 g, 23%).

Analysis Calcd for $C_{17}H_{22}N_2O_2.0.375 H_2O$: C 69.66, H 7.82, N 9.56; found C 69.82, H 7.57, N 9.07.

Example 5 cis-1-Amino-3-cyano-3-(3-cyclopentyloxy-4-methoxyphenyl)cyclobutane

A solution of trans-3-cyano-3-(3-cyclopentyloxy-4-methoxyphenyl)cyclobutan-1-ol (0.13 g, 0.43 mmol) in tetrahydrofuran (5 mL) was treated with phthalimide (0.10 g, 0.65 mmol), triphenylphosphine (0.17 g, 0.65 mmol) and dropwise with diethyl azodicarboxylate (0.11 mL, 0.65 mmol). The reaction was stirred at room temperature under an argon atmosphere for 20 h, was evaporated and was partially purified by flash chromatography, eluting with 3:7 ethyl acetate:hexanes to provide a mixture of cis-3-cyano-3-(3-cyclopentyloxy-4-methoxyphcnyl)-1-phthalimidocyclobutane:phthalimide (~3:1) as a white solid (0.18 g). This intermediate mixture was dissolved in ethanol (2 mL) and tetrahydrofuran (1 mL), was treated with hydrazine monohydrate (0.13 mL, 2.6 mmol) and was stirred at room temperature under an argon atmosphere for 18 h. The reaction was diluted with water and was extracted with three portions of 1:9 methanol:dichloromethane. The organic extract was dried (magnesium sulfate) and evaporated. Purification by flash chromatography, eluting with 1:99 methanol:dichloromethane provided product as a yellow oil (0.04 g, 35%).

Analysis Calcd for $C_{17}H_{22}N_2O_2.0.5 H_2O$: C 69.13, H 7.79, N 9.48; found C 69.06, H 7.43, N 9.33.

Example 6 cis-3-Cyano-3-(3-cyclopentyloxy-4-methoxyphenyl)cyclobutane-1-carboxylic acid 6a 3—Cyano-3-(3-cyclopentyloxy-4-methoxyphenyl)cyclobutan-1-one, 1,3-dioxolane ketal.

To a solution of trimethylsilyl trifluoromethanesulfonate (0.16 mL, 0.79 mmol) in dichloromethane (80 mL) at −78° C. under an argon atmosphere was added 1,2-bis(trimethylsilyloxy)ethane (4.90 mL, 20 mmol) followed by cannula addition of a −78° C. solution of 3-cyano-3-(3-cyclopentyloxy-4-methoxyphenyl)cyclobutan-1-one (5.60 g, 19.6 mmol) in dichloromethane (20 mL). The reaction was stirred for 20 h at room temperature, was treated with solid sodium bicarbonate, was diluted with water and was extracted twice with dichloromethane. The organic extract was dried (magnesium sulfate) and evaporated to provide crude product as a dark amber oil (5.49 g, 85%).

6b 3-(1,3-Dioxolane ketal)-1-(3-cyclopentyloxy-4-methoxyphenyl)cyclobutane-1-carboxaldehyde.

To a solution of 3-cyano-3-(3-cyclopentyloxy-4-methoxyphenyl)cyclobutan-1-one (5.49 g, 16.7 mmol) in 5:95 tetrahydrofuran:tert-butyl methyl ether (100 mL) at −15° C. under an argon atmosphere was dropwise added over 0.5 h a solution of 1 M diisobutylaluminum hydride (25.0 mL, 25 mmol). The reaction was stirred 0.5 h, was quenched with 50% acetic acid (20 mL), was diluted with water and was extracted with two portions of tertbutyl methyl ether. The organic extract was washed with two portions of water and with brine, was dried (magnesium sulfate) and was evaporated. Purification by flash chromatography, eluting with 2:8 ethyl acetate : hexanes provided product as a colorless oil (4.13 g, 74%).

6c 3-(3-Cyclopentyloxy-4-methoxyphenyl)-3-hydroxymethylcyclobutan-1-one.

A solution of 3-(1,3-dioxolane ketal )-1-(3-cyclopentyloxy-4-methoxyphenyl)cyclobutane-1-carboxaldehyde (5.0 g, 15.0 mmol) in 1,2-dimethoxyethane (100 tnL) at 0° C. under an argon atmosphere was treated with sodium borohydride (1.21 g, 31.5 mmol). The reaction was stirred for 0.5 h, was quenched with water and was extracted with three portions of dichloromethane. The organic cataract was dried (magnesium sulfate) and evaporated to provide an intermediate yellow oil (5.25 g).This oil was dissolved in tetrahydrofuran (200 mL) and 10% hydrochloric acid (45 mL) and was stirred at 55–60° C. for 20 h. The reaction was cooled, was poured into 0° C. water and was extracted with three portions of dichloroinethane. The organic extract was dried (magnesium sulfate) and evaporated to provide product as a colorless oil (4.75 g, 100%).

6d 3-Acetoxymethyl-3-(3-cyclopentyloxy-4-methoxyphenyl)cyclobutan-1-one.

A solution of 3-(3-cyclopentyloxy-4-methoxyphenyl)-3-hydroxymethylcyclobutan-1-one (4.75 g, 15 mmol) in dichloromethane (150 mL) was treated with pyridine (4.25 mL, 52.5 mmol) and acetic anhydride (4.25 mL, 45 mmol). The reaction was stirred for 24 h at 30–35° C. under an argon atmosphere, was cooled, was diluted with 1 M hydrochloric acid and was extracted with three portions of dichloromethane. The organic extract was dried (magnesium sulfate) and evaporated. Purification by flash chromatography, eluting with 2:8 ethyl acetate:hexanes provided product as a yellow oil (3.96 g, 79%)

6e 3-(3-Cyclopentyloxy-4-methoxyphenyl)-3-hydroxymethylcyclobutane-1-ketene-(1,3-dithiane) dithioacetal.

To a solution of 2-(trimethylsilyl)-1,3-dithiane (1.25 mL, 6.5 mmol) in tetrahydrofuran (30 mL) it 0° C. under an argon atmosphere was dropwise added a solution of 2.5 M n-butyllithium in hexanes (2.6 mL, 6.5 mmol) followed after 15 min by the rapid addition of a solution of 3-acetoxy methyl-3-(3-cyclopentyloxy-4-methoxyphenyl)cyclobutan-1-one (1.08 g, 3.25 mmol) in tetrahydrofuran (10 mL). The reaction was stirred for 75 min, was quenched with ammonium chloride, was diluted with water and was extracted with three portions of dichloromethane. The organic extract was dried (magnesium sulfate) and evaporated. Purification by flash chromatography, eluting with 2:8 ethyl acetate:hexanes provided product as a yellow oil (0.76 g, 60%).

6f Methyl 3-(3-cyclopentyloxy-4-methoxyphenyl)-3-hydroxymethylcyclobutane-1-carboxylate.

A solution of 3-(3-cyclopentyloxy-4-methoxyphenyl)-3-hydroxymethylcyclobutane-1-ketene-(1,3-dithiane) dithioacetal (1.56 g, 3.97 mmol) in methanol (100 mL) was treated with 70% perchloric acid (1.05 mL, 9 mmol) and mercury(II)chloride (4.3 g, 12 mmol). The reaction was stirred at reflux under an argon atmosphere for 1.5 h, then at room temperature for 20 h, was diluted with dichloromethane, was filtered through Celite, was neutralized with sodium bicarbonate, and was extracted with three portions of dichloromethane. The organic extract was washed with five portions of sodium bisulfite, with water and with brine, was dried (magnesium sulfite) and was evaporated. Purification by flash chromatography, eluting with 4:6 ethyl acetate:hexanes provided product as a colorless oil (0.99 g, 75%). $^1$H-NMR indicated the cis/trans isomer ratio to be ~1:1.

6g Methyl cis-3-carboxaldehyde-3-(3-cyclopentyloxy-4-methoxyphenyl)cyclobutane-1-carboxylate and methyl trans-3-carboxaldehyde-3-(3-cyclopentyloxy-4-methoxyphenyl)cyclobutane-1-carboxylate.

To a suspension of pyridinium chlorochromate (1.09 g, 5.06 mmol) in dichloromethane (50 mL) was rapidly added a solution of methyl 3-(3-cyclopentyloxy-4-methoxyphenyl)-3-hydroxymethylcyclobutane-1-carboxylate (1.13 g, 3.37 mmol) in dichloromethane (20 mL). The reaction was stirred 4 h at room temperature under an argon atmosphere, was filtered through Celite and was evaporated. Purification by flash chromatography, eluting with 1:9 ethyl acetate:hexanes provided both products: Methyl trans-3-carboxaldehyde -3-(3-cyclopentyloxy-4-methoxyphenyl)cyclobutane-1-carboxylate was obtained as a colorless oil (0.36 g, 32%), $R_f$=0.37 (2:8 ethyl acetate:hexanes) and methyl cis-3-carboxaldehyde-3-(3-cyclopentyloxy-4-methoxyphenyl)cyclobutane-1-carboxylate was obtained as a mixture containing ~10% trans isomer, as a white solid, m.p. 43–45° C., (0.20 g, 16%), $R_f$=0.29 (2:8 ethyl acetate:hexanes).

6h Methyl cis -3-(3-cyclopentyloxy-4-methoxyphenyl)-3-oximatocyclobutane-1-carboxylate.

A solution of methyl cis-3-carboxaldehyde-3-(3-cyclopentyloxy-4-methoxyphenyl)cyclobutane-1-carboxylate (0.20 g, 0.60 mmol) in toluene (5 mL) was treated with hydroxylamine hydrochloride (0.04 g, 0.6 mmol) and pyridine (0.05 mL, 1.2 mmol) and several 4A molecular sieves and was heated at reflux under an argon atmosphere for 4 h. The reaction solution was cooled, was treated with hydroxylamine hydrochloride (0.08 g, 1.2 mmol) and pyridine (0.10 mL, 2.4 mmol) and was heated at reflux for 2 h. The reaction was cooled, was diluted with 1 M hydrochloric acid and was extracted with three portions of dichloromethane. The organic extract was dried (magnesium sulfate) and evaporated. Purification by flash chromatography, eluting with 15:85 ethyl acetate: hexanes provided the product as a white solid (0.13 g, 62%), containing ~10% trans isomer (by $^1$H-NMR), m.p. 57–59° C.

6i Methyl cis-3-cyano-3-(3-cyclopentyloxy-4-methoxyphenyl)cyclobutane-1-carboxylate.

A solution of methyl cis-3-(3-cyclopentyloxy-4-methoxyphenyl)-3-oximato-cyclobutane-1-carboxylate (0.13 g, 0.37 mmol) in dichloromethane (3 mL) at −78° C. under an argon atmosphere was treated with triethylamine (0.24 mL, 1.67 mmol) and with a solution of trifluoromethanesulfonic anhydride (0.14 mL, 0.81 mmol) in dichloromethane (2 mL). The reaction was stirred at room temperature for 24 h, was recooled to −78° C. and was treated with triethylamine (0.12 mL, 0.89 mmol) and with a solution of trifluoromethanesulfonic anhydride (0.07 mL, 0.40 mmol) in dichloromethane (2 mL) The reaction was stirred at room temperature for 4 h, was diluted with sodium bicarbonate and water and was extracted with three portions of dichloromethane. The organic extract was dried (magnesium sulfate) and evaporated. Purification by flash chromatography, eluting with 15:85 ethyl acetate:hexanes provided product as a colorless oil (0.12 g, 95%), containing no trace of trans isomer (by $^1$H-NMR).

6j cis-3-Cyano-3-(3-cyclopentyloxy-4-methoxyphenyl) cyclobutane-1-carboxylic acid.

A solution of methyl cis-3-cyano-3-(3-cyclopentyloxy-4-methoxyphenyl)cyclobutane-1-carboxylate (0.12 g, 0.35 mmol) and potassium hydroxide (0.06 g, 1.05 mmol) in tetrahydrofuran (2.5 mL), methanol (2.5 mL) and water (1 mL) was stirred at room temperature for 24 h. The reaction was acidified with 10% hydrochloric acid, was diluted with water, and was extracted with three portions of 5/95 methanol/dichloromethane. The organic extract was dried (magnesium sulfate) and evaporated. Purification by two flash chromatographies, eluting first with 0.2:2:98 acetic acid:methanol:dichloromethane, then with 1:9 methanol:dichloromethane, then triturating from diethyl ether provided product as a waxy white solid (0.10 g, 92%), m.p.77–79° C.

Analysis Calcd for $C_{18}H_{21}NO_4 \cdot 0.8 H_2O$: C 65.56, H 6.59, N 4.25; found: C 65.19, H 6.31, N 4.09.

Example 7 trans-3-Cyano-3-(3-cyclopentyloxy-4-methoxyphenyl)cyclobutane-1-carboxylic acid

7a Methyl trans -3-(3-cyclopentyloxy-4-methoxyphenyl)-3-oximato-cyclobutane-1-carboxylate.

A solution of methyl trans-3-carboxaldehyde-3-(3-cyclopentyloxy-4-methoxyphenyl)cyclobutane-1-carboxylate (0.36 g, 1.07 mmol) (prepared in example 9g) in toluene (5 mL) was treated with hydroxylamine hydrochloride (0.075 g, 1.07 mmol) and pyridine (0.09 mL, 2.14 mmol) and several 4A molecular sieves and was heated at reflux under an argon atmosphere for 4 h. The reaction solution was cooled, was treated with hydroxylamine hydrochloride (0.15 g, 2.14 mmol) and pyridine (0.18 mL, 4.3 mmol) and was heated at reflux for 2 h. The reaction was cooled, was diluted with 1 M hydrochloric acid and was extracted with three portions of dichloromethane. The organic extract was dried (magnesium sulfate) and evaporated. Purification by flash chromatography, eluting with 2:8 ethyl acetate:hexanes provided the product as an off-white solid (0.13 g, 62%), m.p. 115–117° C.

7b Methyl trans-3-cyano-3-(3-cyclopentyloxy-4-methoxyphenyl)cyclobutane-1-carboxylate.

A solution of methyl trans -3-(3-cyclopentyloxy-4-methoxyphenyl)-3-oximato-cyclobutane-1-carboxylate (0.11 g, 0.32 mmol) in dichloromethane (3 mL) at −78° C. under an argon atmosphere was treated with triethylamine (0.10 mL, 0.67 mmol) and with a solution of trifluoromethanesulfonic anhydride (0.06 mL, 0.32 mmol) in dichloromethane (2 mL). The reaction was stirred at room temperature for 3d, was recooled to −78° C. and was again treated with triethylamine (0.10 mL, 0.67 mmol) and with a solution of trifluoromethanesulfonic anhydride (0.06 mL, 0.32 mmol) in dichloromethane (2 mL). The reaction was stirred at room temperature for 4 h, was recooled to −78° C. and was again treated with triethylamine (0.10 mL, 0.67 mmol) and with a solution of trifluoromethanesulfonic anhydride (0.06 mL, 0.32 mmol) in dichloromethane (2 mL) The reaction was stirred at room temperature for 2 h, was diluted with sodium bicarbonate and water and was extracted with three portions of dichloromethane. The organic extract was dried (magnesium sulfate) and evaporated. Purification by flash chromatography, eluting with 1:9 ethyl acetate:hexanes provided product as a colorless oil (0.06 g, 54%).

7c trans-3-Cyano-3-(3-cyclopentyloxy-4-methoxyphenyl)cyclobutane-1-carboxylic acid.

A solution of methyl trans-3-cyano-3-(3-cyclopentyloxy-4-methoxyphenyl)cyclobutane-1-carboxylate (0.06 g, 0.17 mmol) and potassium hydroxide (0.03 g, 0.55 mmol) in tetrahydrofuran (2.5 mL), methanol (2.5 mL) and water (1 mL) was stirred a t room temperature for 20 h. The reaction was acidified with 10% hydrochloric acid, was diluted with water, and was extracted with three portions of 5/95 methanol/dichloromethane. The organic extract was dried (magnesium sulfate) and evaporated. Purification by two flash chromatographies, eluting first with 0.2:2:98 acetic acid:methanol:dichloromethane, then with 3:97 methanol:dichloromethane provided product as a very pale yellow oil (0.03 g, 49%).

UTILITY EXAMPLES

Example A

Inhibitory Effect of Compounds of Formula (I) and (II) on in vitro TNF Production by Human Monocytes The inhibitory effect of compounds of Formula (I) and (II) on in vitro TNF production by human monocytes may be determined by the protocol as described in Badger et al., EPO published Application 0 411 754 A2, Feb. 6, 1991, and in Hanna, WO 90/15534, Dec. 27, 1990.

Example B

Two models of endotoxic shock have been utilized to determine in vivo TNF activity for the compounds of Formula (I) and (II). The protocol used in these models is described in Badger et al., EPO published Application 0 411 754 A2, Feb. 6, 1991, and in Hanna, WO 90/15534, Dec. 27, 1990.

The compound of Example 1 herein demonstrated a positive in vivo response in reducing serum levels of TNF induced by the injection of endotoxin.

Example C

Isolation of PDE Isozymes

The phosphodiesterase inhibitory activity and selectivity of the compounds of Formula (I) and (II) can be determined using a battery of five distinct PDE isozymes. The tissues used as Sources of the different isozymes are as follows: 1) PDE Ib, porcine aorta; 2) PDE Ic, guinea-pig heart; 3) PDE III, guinea-pig heart; 4) PDE 4, human monocyte; and 5) PDE V (also called "Ia"), canine trachealis. PDEs Ia, Ib, Ic and III are partially purified using standard chromatographic techniques [Torphy and Cieslinski, Mol. Pharmacol., 37:206–214, 1990]. PDE 4 is purified to kinetic homogeneity by the sequential use of anion-exchange followed by heparin-Sepharose chromatography [Torphy et al., J. Biol. Chem., 267:1798–1804, 1992].

Phosphodiesterase activity is assayed as described in the protocol of Torphy and Cieslinski, Mol. Pharmacol., 37:206–214, 1990. Positive $IC_{50}$'s in the nanomolar to $\mu M$ range for compounds of the workings examples described herein for Formula (I) and (II) have been demonstrated.

What is claimed is:

1. A compound of Formula (I):

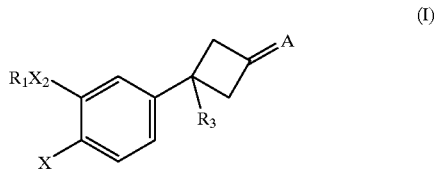

wherein:
R$_1$ is —(CR$_4$R$_5$)$_n$C(O)O(CR$_4$R$_5$)$_m$R$_6$, —(CR$_4$R$_5$)$_n$C(O)NR$_4$(CR$_4$R$_5$)$_m$R$_6$, —(CR$_4$R$_5$)$_n$O(CR$_4$R$_5$)$_m$R$_6$, or —(CR$_4$R$_5$)$_r$R$_6$ wherein the alkyl moieties may be unsubstituted or substituted with one or more fluorines;
m is 0 to 2;
n is 1 to 4;
r is 0 to 6;
R$_4$ and R$_5$ are independently hydrogen or C$_{1-2}$ alkyl;
R$_6$ is hydrogen, methyl, hydroxyl, aryl, halo substituted aryl, aryloxy C$_{1-3}$ alkyl, halo substituted aryloxy C$_{1-3}$ alkyl, indanyl, indenyl, C$_{7-11}$ polycycloalkyl C$_{3-6}$ cycloalkyl, or a C$_{4-6}$ cycloalkyl containing one or two unsaturated bonds, wherein the cycloalkyl or heterocyclic moiety may be unsubstituted or substituted by 1 to 3 methyl groups, one ethyl group or an hydroxyl group;
provided that:
a) when R$_6$ is hydroxyl, then m is 2; or
b) when R$_6$ is hydroxyl, then r is 2 to 6; or
c) when R$_6$ is 2-tetrahydropyranyl, 2-tetrahydrothiopyranyl, 2-tetrahydrofuranyl, or 2-tetrahydrothienyl, then m is 1 or 2; or d) when $R_6$ is 2-tetrahydropyranyl, 2-tetrahydrothiopyranyl, 2-tetrahydrofuranyl, or 2-tetrahydrothienyl, then r is 1 to 6;
e) when n is 1 and m is 0, then $R_6$ is other than H in —$(CR_4R_5)_nO(CR_4R_5)_mR_6$;

X is $VR_2$, halogen, nitro, $NR_4R_5$, or formyl amine;
V is O or $S(O)_{m'}$;
m' is 0, 1, or 2;
$X_2$ is O or $NR_8$;
$R_2$ is —$CH_3$ or —$CH_2CH_3$ unsubstituted or substituted by 1 or more fluorines;
$R_3$ is halogen, $C_{1-4}$ alkyl, halo-substituted $C_{1-4}$ alkyl, $CH_2NHC(O)C(O)NH_2$, —$CH=CR_8R_{8'}$, cyclopropyl optionally substituted by $R_{8'}$, CN, $OR_8$, $CH_2OR_8$, $NR_8R_{10}$, $CH_2NR_8R_{10}$, $C(Z)H$, $C(O)OR_8$, $C(O)NR_8R_{10}$, or $C\equiv CR_8$;
Z is O, $NR_9$, $NOR_8$, NCN, $C(-CN)_2$, $CR_8CN$, $CR_8NO_2$, $CR_8C(O)OR_8$, $CR_8C(O)NR_8R_8$, $C(-CN)NO_2$, $C(-CN)C(O)OR_9$, $C(-CN)C(O)NR_8R_8$;
A is O, $NR_7$, $NCR_4R_5C_{2-6}$ alkenyl, $NOR_{14}$, $NOR_{15}$, $NOCR_4R_5C_{2-6}$ alkenyl, $NNR_4R_{14}$, $NNR_4R_{15}$, NCN, $NNR_8C(O)NR_8R_{14}$, $NNR_8C(S)NR_8R_{14}$;
$R_7$ is —$(CR_4R_5)_qR_{12}$ or $C_{1-6}$ alkyl wherein the $R_{12}$ or $C_{1-6}$ alkyl group is unsubstituted or substituted one or more times by methyl or ethyl unsubstituted or substituted by 1–3 fluorines, —F, —Br, —Cl, —$NO_2$, —$NR_{10}R_{11}$, —$C(O)R_8$, —$CO_2R_8$, —$O(CH_2)_qR_8$, —CN, —$C(O)NR_{10}R_{11}$, —$O(CH_2)_qC(O)NR_{10}R_{11}$, —$O(CH_2)_qC(O)R_8$, —$NR_{10}C(O)NR_{10}R_{11}$, —$NR_{10}C(O)R_{11}$, —$NR_{10}C(O)OR_9$, —$NR_{10}C(O)R_{13}$, —$C(NR_{10})NR_{10}R_{11}$, —$C(NCN)NR_{10}R_{11}$, —$C(NCN)SR_9$, —$NR_{10}C(NCN)SR_9$, —$NR_{10}C(NCN)NR_{10}R_{11}$, $NR_{10}S(O)_2R_9$, —$S(O)_{m'}R_9$, —$NR_{10}C(O)C(O)NR_{10}R_{11}$, —$NR_{10}C(O)C(O)R_{10}$, or $R_{13}$;
q is 0, 1, or 2;
$R_{12}$ is $R_{13}$, $C_3-C_7$ cycloalkyl, (2-, 3- or 4-pyridyl), pyrimidyl, pyrazolyl, (1- or 2-imidazolyl), pyrrolyl, piperazinyl, piperidinyl, morpholinyl, furanyl, (2- or 3-thienyl), quinolinyl, naphthyl, or phenyl;
$R_8$ is hydrogen or $R_9$;
$R_{8'}$ is $R_8$ or fluorine;
$R_9$ is $C_{1-4}$ alkyl unsubstituted or substituted by one to three fluorines;
$R_{10}$ is $OR_8$ or $R_{11}$;
$R_{11}$ is hydrogen, or $C_{1-4}$ alkyl unsubstituted or substituted by one to three fluorines; or when $R_{10}$ and $R_{11}$ are as $NR_{10}R_{11}$ they may together with the nitrogen form a 5 to 7 membered ring comprised only of carbon atoms or carbon atoms and at least one heteroatom selected from O, N, or S;
$R_{13}$ is oxazolidinyl, oxazolyl, thiazolyl, pyrazolyl, triazolyl, tetrazolyl, imidazolyl, imidazolidinyl, thiazolidinyl, isoxazolyl, oxadiazolyl, or thiadiazolyl, and each of these heterocyclic rings is connected through a carbon atom and each may be unsubstituted or substituted by one or two $C_{1-2}$ alkyl groups;
$R_{14}$ is hydrogen or $R_7$; or when $R_8$ and $R_{14}$ are as $NR_8R_{14}$ they may together with the nitrogen form a 5 to 7 membered ring comprised only of carbon atoms or carbon atoms and at least one heteroatom selected from O, N, or S; provided that:
$R_{15}$ is $C(O)R_{14}$, $C(O)NR_4R_{14}$, $S(O)_2R_7$, or $S(O)_2NR_4R_{14}$;
or a pharmaceutically acceptable salt thereof.

2. A compound of claim 1 wherein wherein $R_1$ is —$CH_2$-cyclopropyl, cyclopentyl, 3-hydroxycyclopentyl, methyl or $CF_2H$; X is $VR_2$; V is oxygen; $X_2$ is oxygen; $R_2$ is $CF_2H$ or methyl, $R_3$ is —$CH=CR_{8'}$, $R_{8'}$, $C\equiv CR_8$ or CN; and A is O or $NR_7$.

3. A compound of Formula (I) according to claim 2 which is 3-acetoxymethyl-3-(3-cyclopentyloxy-4-methoxyphenyl)cyclobutan-1-one, or 3-cyano-3-(3-cyclopentyloxy-4-methoxyphenyl)cyclobutan-1-one, or 3-(3-cyclopentyloxy-4-methoxyphenyl)-3-hydroxymethylcyclobutane-1-ketene-(1,3-dithiane) dithioacetal.

4. A compound of Formula (II)

(II)

wherein:
$R_1$ is —$(CR_4R_5)_nC(O)O(CR_4R_5)_mR_6$, —$(CR_4R_5)_nC(O)NR_4(CR_4R_5)_mR_6$, —$(CR_4R_5)_nO(CR_4R_5)_mR_6$, or —$(CR_4R_5)_rR_6$ wherein the alkyl moieties may be unsubstituted or substituted with one or more fluorines;
m is 0 to 2;
n is 1 to 4;
r is 0 to 6;
$R_4$ and $R_5$ are independently hydrogen or $C_{1-2}$ alkyl;
$R_6$ is hydrogen, methyl, hydroxyl, aryl, halo substituted aryl, aryloxy $C_{1-3}$ alkyl, halo substituted aryloxy $C_{1-3}$ alkyl, indanyl, indenyl, $C_{7-11}$ polycycloalkyl $C_{3-6}$ cycloalkyl, or a $C_{4-6}$ cycloalkyl containing one or two unsaturated bonds, wherein the cycloalkyl or heterocyclic moiety may be unsubstituted or substituted by 1 to 3 methyl groups, one ethyl group or an hydroxyl group;
provided that:
a) when $R_6$ is hydroxyl, then m is 2; or
b) when $R_6$ is hydroxyl, then r is 2 to 6; or
c) when $R_6$ is 2-tetrahydropyranyl, 2-tetrahydrothiopyranyl, 2-tetrahydrofuranyl, or 2-tetrahydrothienyl, then m is 1 or 2; or
d) when $R_6$ is 2-tetrahydropyranyl, 2-tetrahydrothiopyranyl, 2-tetrahydrofuranyl, or 2-tetrahydrothienyl, then r is 1 to 6;
e) when n is 1 and m is 0, then $R_6$ is other than H in —$(CR_4R_5)_nO(CR_4R_5)_mR_6$;

X is $VR_2$, halogen, nitro, $NR_4R_5$, or formyl amine;
V is O or $S(O)_{m'}$;
m' is 0, 1, or 2;
$X_2$ is O or $NR_8$;
$R_2$ is —$CH_3$ or —$CH_2CH_3$ unsubstituted or substituted by 1 or more fluorines;
$R_3$ is halogen, $C_{1-4}$ alkyl, halo-substituted $C_{1-4}$ alkyl, $CH_2NHC(O)C(O)NH_2$, —$CH=CR_8R_{8'}$, cyclopropyl optionally substituted by $R_{8'}$, CN, $OR_8$, $CH_2OR_8$, $NR_8R_{10}$, $CH_2NR_8R_{10}$, $C(Z)H$, $C(O)OR_8$, $C(O)NR_8R_{10}$, or $C\equiv CR_8$;
Z is O, $NR_9$, $NOR_8$, NCN, $C(-CN)_2$, $CR_8CN$, $CR_8NO_2$, $CR_8C(O)OR_8$, $CR_8C(O)NR_8R_8$, $C(-CN)NO_2$, $C(-CN)C(O)OR_9$, $C(-CN)C(O)NR_8R_8$;
B is $OR_{14}$, $OR_{15}$, $SR_{14}$, $S(O)_mR_7$, $S(O)_2NR_{10}R_{14}$, $NR_{10}R_{14}$, $NR_{14}C(O)R_9$, $NR_{10}C(Y')R_{14}$, $NR_{10}C(O)$ $OR_7$, $NR_{10}C(Y')NR_{10}R_{14}$, $NR_{10}S(O)_2NR_{10}R_{14}$, $NR_{10}C(NCN)NR_{10}R_{14}$, $NR_{10}S(O)_2R_7$, $NR_{10}C(CR_4NO_2)NR_{10}R_{14}$, $NR_{10}C(NCN)SR_9$, $NR_{10}C(CR_4NO_2)SR_9$, $NR_{10}C(NR_{10})NR_{10}R_{14}$, $NR_{10}C(O)C(O)NR_{10}R_{14}$, or $NR_{10}C(O)C(O)OR_{14}$; or B is $C(Y')R_{14}$, $C(O)OR_{14}$, $C(Y')NR_{10}R_{14}$, $C(NR_{10})NR_{10}R_{14}$, CN, $C(NOR_8)R_{14}$, $C(NOR_{14})R_8$, $C(NR_8)NR_{10}R_{14}$, $C(NR_{14})NR_8R_8$, $C(NCN)NR_{10}R_{14}$, $C(NCN)SR_{11}$, (2-, 4- or 5-imidazolyl), (3-, 4- or 5-pyrazolyl), (4- or 5-triazolyl[1,2,3]), (3- or 5-triazolyl[1,2,4]), (5-tetrazolyl), (2-, 4- or 5-oxazolyl), (3-, 4- or 5-isoxazolyl), (3- or 5-oxadiazolyl[1,2,4]), (2-oxadiazolyl[1,3,4]), (2-thiadiazolyl[1,3,4]), (2-, 4- or 5-thiazolyl), (2-, 4- or 5-oxazolidinyl), (2-, 4- or 5-thiadiazolinyl), or (2-, 4- or 5-imidazolidinyl): wherein all of the heterocyclic ring systems may be optionally substituted one or more times by $R_{14}$;

Y' is O or S;

$R_7$ is $-(CR_4R_5)_qR_{12}$ or $C_{1-6}$ alkyl wherein the $R_{12}$ or $C_{1-6}$ alkyl group is unsubstituted or substituted one or more times by methyl or ethyl unsubstituted or substituted by 1–3 fluorines, —F, —Br, —Cl, —$NO_2$, —$NR_{10}R_{11}$, —$C(O)R_8$, —$CO_2R_8$, —$(CH_2)_qR_8$, —CN, —$C(O)NR_{10}R_{11}$, —$O(CH_2)_qC(O)NR_{10}R_{11}$, —$O(CH_2)_qC(O)R_8$, —$NR_{10}C(O)NR_{10}R_{11}$, —$NR_{10}C(O)R_{11}$, —$NR_{10}C(O)OR_9$, —$NR_{10}C(O)R_{13}$, —$C(NR_{10})NR_{10}R_{11}$, —$C(NCN)NR_{10}R_{11}$, —$C(NCN)SR_9$, —$NR_{10}C(NCN)SR_9$, —$NR_{10}C(NCN)NR_{10}R_{11}$, —$NR_{10}S(O)_2R_9$, —$S(O)_mR_9$, —$NR_{10}C(O)C(O)NR_{10}R_{11}$, —$NR_{10}C(O)C(O)R_{10}$, or $R_{13}$;

q is 0, 1, or 2;

$R_{12}$ is $R_{13}$, $C_3$–$C_7$ cycloalkyl, (2-, 3- or 4-pyridyl), pyrimidyl, pyrazolyl, (1- or 2-imidazolyl), pyrrolyl, piperazinyl, piperidinyl, morpholinyl, furanyl, (2- or 3-thienyl), quinolinyl, naphthyl, or phenyl;

$R_8$ is hydrogen or $R_9$;

$R_{8'}$ is $R_8$ or fluorine;

$R_9$ is $C_{1-4}$ alkyl unsubstituted or substituted by one to three fluorines;

$R_{10}$ is $OR_8$ or $R_{11}$;

$R_{11}$ is hydrogen, or $C_{1-4}$ alkyl unsubstituted or substituted by one to three fluorines; or when $R_{10}$ and $R_{11}$ are as $NR_{10}R_{11}$ they may together with the nitrogen form a 5 to 7 membered ring comprised only of carbon atoms or carbon atoms and at least one heteroatom selected from O, N, or S;

$R_{13}$ is oxazolidinyl, oxazolyl, thiazolyl, pyrazolyl, triazolyl, tetrazolyl, imidazolyl, imidazolidinyl, thiazolidinyl, isoxazolyl, oxadiazolyl, or thiadiazolyl, and each of these heterocyclic rings is connected through a carbon atom and each may be unsubstituted or substituted by one or two $C_{1-2}$ alkyl groups;

$R_{14}$ is hydrogen or $R_7$; or when $R_8$ and $R_{14}$ are as $NR_8R_{14}$ they may together with the nitrogen form a 5 to 7 membered ring comprised only of carbon atoms or carbon atoms and at least one heteroatom selected from O, N, or S; provided that:

$R_{15}$ is $C(O)R_{14}$, $C(O)NR_4R_{14}$, $S(O)_2R_7$, or $S(O)_2NR_4R_{14}$; provided that:

(f) When $R_{12}$ is N-pyrazolyl, N-imidazolyl, N-triazolyl, N-pyrrolyl, N-piperazinyl, or N-morpholinyl, then q is not 1;

or a pharmaceutically acceptable salt thereof.

5. A compound of Formula (II) according to claim 4 wherein $R_1$ is —$CH_2$-cyclopropyl, cyclopentyl, 3-hydroxycyclopentyl, methyl or $CF_2H$; X is $VR_2$; V is oxygen; $X_2$ is oxygen; $R_2$ is $CF_2H$ or methyl, $R_3$ is CN, and B is $OR_{14}$, $NR_{10}R_{14}$, $OR_{15}$, or $C(O)OR_{14}$.

6. A compound of Formula (II) according to claim 5 which is:

cis-3-cyano-3-(3-cyclopentyloxy-4-methoxyphenyl) cyclobutan-1-ol, trans-3-canto)-3-(3-cyclopentyloxy-4-methoxyphenyl) cyclobutan-1-ol, trans-1-amino-3-cyano-3-(3-cyclopentyloxy-4-methoxyphenyl)cyclobutane cis-1-amino-3-cyano-3-(3-cyclopentyloxy-4-methoxyphenyl)cyclobutane, cis-3-cyano-3-(3-cyclopentyloxy-4-methoxyphenyl) cyclobutane-1-carboxylic acid methyl 3-(3-cyclopentyloxy-4-methoxyphenyl)-3-hydroxymethylcyclobutane-1-carboxylate, methyl cis-3-carboxaldehyde-3-(3-cyclopentyloxy-4-methoxyphenyl)cyclobutane-1-carboxylate, methyl trans-3-carboxaldehyde-3-(3-cyclopentyloxy-4-methoxyphenyl)cyclobutane-1-carboxylate, methyl cis-3-(3-cyclopentyloxy-4-methoxyphenyl)-3-oximatocyclobutane-1-carboxylate, methyl cis-3-cyano-3-(3-cyclopentyloxy-4-methoxyphenyl)cyclobutane-1-carboxylate, cis-3-cyano-3-(3-cyclopentyloxy-4-methoxyphenyl) cyclobutane-1-carboxylic acid, or trans-3-cyan)-3-(3-cyclopentyloxy-4-methoxyphenyl) cyclobutane-1-carboxylic acid.

7. A pharmaceutical composition comprising a pharmaceutically acceptable excipient and a compound of Formula (I) according to claim 1.

8. A pharmaceutical composition comprising a pharmaceutically acceptable excipient and a compound of Formula (I) according to claim 4.

9. A method for treating asthma or chronic obstructive pulmonary disease (COPD) comprising administering a compound of Formula (I) according to claim 1 in an amount sufficient to treat asthma or COPD in a human.

10. A method for treating as asthma or chronic obstructive pulmonary disease (COPD) comprising administering a compound of Formula (II) according to claim 4 in an amount sufficient to treat asthma or COPD in a human.

* * * * *